United States Patent
Thienphrapa et al.

(10) Patent No.: US 11,887,236 B2
(45) Date of Patent: Jan. 30, 2024

(54) ANIMATED POSITION DISPLAY OF AN OSS INTERVENTIONAL DEVICE

(71) Applicant: KONINKLIJKE PHILIPS N.V., Eindhoven (NL)

(72) Inventors: Paul Thienphrapa, Cambridge, MA (US); Neriman Nicoletta Kahya, Eindhoven (NL); Olivier Pierre Nempont, Suresnes (FR); Pascal Yves François Cathier, Asnieres-sur-Seine (FR); Molly Lara Flexman, Melrose, MA (US); Torre Michelle Bydlon, Melrose, MA (US); Raoul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 278 days.

(21) Appl. No.: 16/957,796

(22) PCT Filed: Dec. 29, 2018

(86) PCT No.: PCT/EP2018/097145
§ 371 (c)(1),
(2) Date: Jun. 25, 2020

(87) PCT Pub. No.: WO2019/134898
PCT Pub. Date: Jul. 11, 2019

(65) Prior Publication Data
US 2020/0402286 A1 Dec. 24, 2020

Related U.S. Application Data

(60) Provisional application No. 62/612,747, filed on Jan. 2, 2018.

(51) Int. Cl.
*G06T 13/80* (2011.01)
*A61B 34/20* (2016.01)
(Continued)

(52) U.S. Cl.
CPC ............ *G06T 13/80* (2013.01); *A61B 5/6847* (2013.01); *A61B 5/744* (2013.01); *A61B 34/20* (2016.02);
(Continued)

(58) Field of Classification Search
CPC ............ A61B 34/20; A61B 2034/2061; A61B 5/6847; A61B 5/744; A61B 1/00;
(Continued)

(56) References Cited

U.S. PATENT DOCUMENTS 8,554,306 B2  10/2013 Maier
9,078,567 B2   7/2015 Fuimaono
(Continued)

FOREIGN PATENT DOCUMENTS

WO  2003094114  11/2003
WO  2015049142   4/2015
(Continued)

OTHER PUBLICATIONS

Mandal et al., "Vessel-based registration of an optical shape sensing catheter for MR navigation", 2016 (Year: 2016).*
(Continued)

*Primary Examiner* — Phong X Nguyen

(57) ABSTRACT

An OSS animated display system for an interventional device (40) including an integration of one or more optical shape sensors and one or more interventional tools. The OSS animated display system employs a monitor (121) and a display controller (110) for controlling a real-time display on the monitor (121) of an animation of a spatial positional relationship between the OSS interventional device (40) and an object (50). The display controller (110) derives the animation of the spatial positional relationship between the OSS interventional device (40) and the object (50) from a shape of the optical shape sensor(s).

20 Claims, 14 Drawing Sheets

(51) Int. Cl.
*A61B 5/00* (2006.01)
*A61B 1/00* (2006.01)
*A61B 1/267* (2006.01)
*A61B 8/12* (2006.01)
*A61B 17/3207* (2006.01)
*A61B 17/84* (2006.01)
*A61B 17/88* (2006.01)
*A61F 2/82* (2013.01)
*A61M 25/00* (2006.01)
*A61M 25/09* (2006.01)

(52) U.S. Cl.
CPC ............... *A61B 1/00* (2013.01); *A61B 1/2676* (2013.01); *A61B 8/12* (2013.01); *A61B 17/3207* (2013.01); *A61B 17/848* (2013.01); *A61B 17/8875* (2013.01); *A61B 2034/2055* (2016.02); *A61B 2034/2061* (2016.02); *A61F 2/82* (2013.01); *A61M 25/00* (2013.01); *A61M 25/09* (2013.01)

(58) Field of Classification Search
CPC ..... A61B 1/2676; A61B 8/12; A61B 17/3207; A61B 17/848; A61B 17/8875; A61B 2034/2055; G06T 13/80; A61F 2/82; A61M 25/00; A61M 25/09; G16H 30/20
See application file for complete search history.

(56) References Cited

U.S. PATENT DOCUMENTS

| | | | |
|---|---|---|---|
| 9,375,141 | B2 | 6/2016 | Trumer |
| 10,219,863 | B2* | 3/2019 | Yu ........................... A61B 18/20 |
| 11,071,449 | B2* | 7/2021 | Heeren ................ A61B 3/1005 |
| 11,259,774 | B2* | 3/2022 | Bharat ................. A61N 5/1007 |
| 2008/0234576 | A1 | 9/2008 | Gavit-Houdant |
| 2008/0262297 | A1* | 10/2008 | Gilboa .................. A61B 90/57 |
| | | | 600/109 |
| 2010/0030063 | A1 | 2/2010 | Lee |
| 2013/0303890 | A1 | 11/2013 | Duindam |
| 2014/0276394 | A1* | 9/2014 | Wong ..................... A61B 34/30 |
| | | | 604/95.04 |
| 2016/0101263 | A1* | 4/2016 | Blumenkranz ...... A61B 5/6852 |
| | | | 600/117 |
| 2016/0183841 | A1 | 6/2016 | Duindam |
| 2016/0206381 | A1* | 7/2016 | Grass ..................... A61B 34/20 |
| 2016/0228032 | A1* | 8/2016 | Walker .................. A61B 34/20 |
| 2016/0242855 | A1* | 8/2016 | Fichtinger ...... A61B 17/320016 |
| 2017/0105701 | A1* | 4/2017 | Pelissier ................. A61B 8/565 |
| 2017/0151027 | A1* | 6/2017 | Walker .................. A61B 34/30 |
| 2017/0215973 | A1* | 8/2017 | Flexman ............... A61B 34/20 |
| 2017/0231714 | A1* | 8/2017 | Kosmecki ............. A61B 34/20 |
| | | | 345/419 |
| 2017/0303889 | A1* | 10/2017 | Grim .................. A61B 10/0266 |
| 2017/0319302 | A1* | 11/2017 | Mozes ................... A61B 90/50 |
| 2018/0014889 | A1* | 1/2018 | Denissen ............... A61B 34/20 |
| 2018/0347998 | A1* | 12/2018 | Rossi ................. G01C 21/3476 |
| 2019/0223959 | A1* | 7/2019 | Van Der Linde ...... G01H 9/004 |
| 2019/0380792 | A1* | 12/2019 | Poltaretskyi ............ G06N 3/08 |
| 2020/0197099 | A1* | 6/2020 | Xu .......................... A61B 34/20 |
| 2020/0214768 | A1* | 7/2020 | Baumann ........... A61B 17/3403 |
| 2020/0402286 | A1* | 12/2020 | Thienphrapa ........ A61B 5/6847 |

FOREIGN PATENT DOCUMENTS

| | | |
|---|---|---|
| WO | 2016004177 | 1/2016 |
| WO | 2016041793 | 3/2016 |
| WO | 2016/088037 | 6/2016 |
| WO | 2016/131637 | 8/2016 |
| WO | 2016206975 | 12/2016 |

OTHER PUBLICATIONS

Citardi et al., Augmented Reality for Endoscopic Sinus Surgery With Surgical Navigation: A Cadaver Study, 2016 (Year: 2016).*
Janjic et al., 3D Imaging with a Single-Element Forward-Looking Steerable IVUS Catheter: initial testing, 2016 (Year: 2016).*
International Search Report and Written Opinion dated Apr. 12, 2019 for International Application No. PCT/EP2016/097145 Filed Dec. 29, 2018.

* cited by examiner

ANIMATED POSITION DISPLAY OF AN OSS INTERVENTIONAL DEVICE

CROSS REFERENCE TO RELATED APPLICATIONS

This application is the U.S. National Phase application under 35 U.S.C. § 371 of International Application No. PCT/EP2018/097145 filed Dec. 29, 2018, published as WO 2019/134898 on Jul. 11, 2019, which claims the benefit of U.S. Provisional Patent Application No. 62/612,747 filed Jan. 2, 2018. These applications are hereby incorporated by reference herein.

FIELD OF THE INVENTION

The inventions of the present disclosure generally relate to a real-time display of images illustrative of a tracked position of an interventional device within an anatomical region based on optical shape sensing (OSS) technology.

The inventions of the present disclosure more particularly relate to an animation of the real-time display of images illustrative of a tracked position of an interventional device within an anatomical region based on optical shape sensing technology to thereby provide a visualization of the tracked position of the interventional device relative to an anatomical landmark or another OSS interventional device.

BACKGROUND OF THE INVENTION

Endovascular procedures typically rely on fluoroscopic imaging throughout the procedure to track a position (i.e., a location and/or orientation) of an interventional tool within an anatomical region, where a fluoroscopic imaging field of view is manually updated throughout the procedure to keep the interventional tool within the fluoroscopic imaging field of view.

Alternative or supplemental to fluoroscopic imaging tracking, position tracking technology as known in the art of the present disclosure may be utilized for tracking a position (i.e., a location and/or orientation) of an interventional tool within an anatomical region.

For example, optical shape sensing (OSS) technology uses light along a single core or a multicore optical fiber for device localization and navigation during surgical intervention. The principle involved makes use of distributed strain measurements in the optical fiber using characteristic Rayleigh backscatter or controlled grating patterns. The shape along the optical fiber begins at a specific point along the sensor, known as the launch or z=0, and the subsequent shape position and orientation of the optical fiber are relative to that point.

An OSS fiber may be integrated into an interventional tool (e.g., vascular tools, endoluminal tools and orthopedic tools) to thereby provide live visual guiding via a monitor of the interventional tool during a minimally invasive procedure (e.g., an endovascular procedure) whereby the integrated OSS fiber provides a position (i.e., a location and/or an orientation) of a portion or an entirety of the interventional tool.

A key feature of shape sensing of an optical fiber is that it provides three-dimensional ("3D") information about the entire shape of a device having the optical fiber embedded therein. A challenge is how to properly visualize and communicate the 3D information of the optically shaped sensed interventional tool to a navigator of the interventional tool.

SUMMARY OF THE INVENTION

To improve upon prior systems, controllers and methods for displaying a navigation of an interventional tool within an anatomical region during an interventional procedure of any type, the present disclosure provides inventions for an animated display of images illustrative of a navigation of the interventional device within the anatomical region based on optical shape sensing information of a position (i.e., a location and/or an orientation) of the interventional device within the anatomical region.

One embodiment of the inventions of the present disclosure is an OSS animated display system for an interventional device including an integration of one or more optical shape sensors and one or more interventional tools. The OSS animated display system employs a monitor and a display controller for controlling a real-time display on the monitor of an animation of a spatial positional relationship between the OSS interventional device and an object. The display controller is configured to derive the animation of the spatial positional relationship between the OSS interventional device and the object from a shape of the optical shape sensor.

A second embodiment of the inventions of the present disclosure the display controller employing an image animator configured to derive the animation of the spatial positional relationship between the OSS interventional device and the object from a shape of the optical shape sensor(s), and an image displayer configured to control the real-time display on the monitor of the animation of a spatial positional relationship between the OSS interventional device and an object.

A third embodiment of the inventions of the present disclosure is an OSS animated display method involving the display controller deriving the animation of the spatial positional relationship between the OSS interventional device and the object from a shape of the optical shape sensor(s), and the display controller controlling a real-time display on a monitor of an animation of the spatial positional relationship between the OSS interventional device and the object derived by the display controller.

For purposes of describing and claiming the inventions of the present disclosure:

(1) terms of the art of the present disclosure including, but not limited to, "monitor", "imaging modality", "registration" and "real-time" are to be interpreted as known in the art of the present disclosure and exemplary described in the present disclosure;

(2) the term "anatomical region" broadly encompasses, as known in the art of the present disclosure and exemplary described in the present disclosure, one or more anatomical systems with each anatomical system having a natural or a surgical structural configuration for a navigation of an interventional device therein. Examples of an anatomical region include, but are not limited to, an integumentary system (e.g., skin and appendages), a skeletal system, a muscular system, a nervous system, an endocrine system (e.g., glands and pancreas), a digestive system (e.g., stomach, intestines, and colon), a respiratory system (e.g., airways and lungs), a circulatory system (e.g., heart and blood vessels), a lymphatic system (e.g., lymph nodes), a urinary system (e.g., kidneys), and reproductive system (e.g., uterus);

(3) the term "interventional tool" is to be broadly interpreted as known in the art of the present disclosure including interventional tools known prior to and conceived after the present disclosure. Examples of an interventional tool include, but are not limited to, vascular interventional tools (e.g., guidewires, catheters, stents sheaths, balloons, atherectomy catheters, IVUS imaging probes, deployment systems, etc.), endoluminal interventional tools (e.g., endoscopes, bronchoscopes, etc.) and orthopedic interventional tools (e.g., k-wires and screwdrivers);

(4) the term "OSS sensor" broadly encompasses an optical fiber configured, as known in the art of the present disclosure and hereinafter conceived, for extracting high density strain measurements of the optical fiber derived from light emitted into and propagated through the optical fiber and reflected back within the optical fiber in an opposite direction of the propagated light and/or transmitted from the optical fiber in a direction of the propagated light. An example of an OSS sensor includes, but is not limited to, an optical fiber configured under the principle of Optical Frequency Domain Reflectometry (OFDR) for extracting high density strain measurements of the optical fiber derived from light emitted into and propagated through the optical fiber and reflected back within the optical fiber in an opposite direction of the propagated light and/or transmitted from the optical fiber in a direction of the propagated light via controlled grating patterns within the optical fiber (e.g., Fiber Bragg Grating), a characteristic backscatter of the optical fiber (e.g., Rayleigh backscatter) or any other arrangement of reflective node element(s) and/or transmissive node element(s) embedded, etched, imprinted, or otherwise formed in the optical fiber;

(5) "an integration of one or more optical shape sensors and one or more interventional tools" broadly encompasses any type of combining, adjoining, attaching, mounting, insertion, intermingling or otherwise integrating of optical shape sensor(s) into interventional tool(s) to form an interventional device as understood in the art of the present disclosure and exemplary described in the present disclosure. Examples of such an integration include, but are not limited to, a fixed insertion of optical shape sensor(s) within a channel of a catheter and a guidewire incorporating optical shape sensor(s);

(6) the term "optical shape sensing animated display system" broadly encompasses, as known in the art of the present disclosure and hereinafter conceived, all interventional systems utilized in interventional procedures incorporating the inventive principles of the present disclosure for an animated display of images illustrative of a navigation of the interventional device within based on optical shape sensing information of a position (i.e., a location and/or an orientation) of the interventional device within the anatomical region. Examples of such interventional systems include all interventional systems commercially offered for sale and sold by Philips as known in the art of the present disclosure that hereinafter incorporate the inventive principles of the present disclosure;

(7) the term "optical shape sensing animated display method" broadly encompasses, as known in the art of the present disclosure and hereinafter conceived, all interventional methods utilized in interventional procedures incorporating the inventive principles of the present disclosure for an animated display of images illustrative of a navigation of the interventional device within based on optical shape sensing information of a position (i.e., a location and/or an orientation) of the interventional device within the anatomical region. Examples of such interventional methods include all interventional methods commercially offered for sale and sold by Philips as known in the art of the present disclosure that hereinafter incorporate the inventive principles of the present disclosure;

(8) the term "controller" broadly encompasses all structural configurations of an application specific main board or an application specific integrated circuit for controlling an application of various inventive principles of the present disclosure related to an automatic display of a real-time display of images illustrative of a navigation of the interventional device within the anatomical region based on optical shape sensing (OSS) technology information of a position (i.e., a location and/or an orientation) of the interventional device within the anatomical region as subsequently exemplarily described in the present disclosure. The structural configuration of the controller may include, but is not limited to, processor(s), computer-usable/computer readable storage medium(s), an operating system, application module(s), peripheral device controller(s), interface(s), bus(es), slot(s) and port(s). The labels "OSS sensor", "OSS shape" and "display" as used in the present disclosure for the term "controller" distinguishes for identification purposes a particular controller from other controllers as described and claimed herein without specifying or implying any additional limitation to the term "controller".

(9) the term "application module" broadly encompasses a component of a controller consisting of an electronic circuit and/or an executable program (e.g., executable software and/or firmware stored on non-transitory computer readable medium(s)) for executing a specific application. The labels "Shape Reconstructor", "Image animator" and "Image Displayer" used herein for the term "module" distinguishes for identification purposes a particular module from other modules as described and claimed herein without specifying or implying any additional limitation to the term "application module"; and

(10) the terms "signal", "data", and "command" broadly encompasses all forms of a detectable physical quantity or impulse (e.g., voltage, current, or magnetic field strength) as understood in the art of the present disclosure and as exemplary described in the present disclosure for communicating information and/or instructions in support of applying various inventive principles of the present disclosure as subsequently described in the present disclosure. Signal/data/command communication between components of the present disclosure may involve any communication method, as known in the art of the present disclosure and hereinafter conceived, including, but not limited to, signal/data/command transmission/reception over any type of wired or wireless medium/datalink and a reading of signal/data/command uploaded to a computer-usable/computer readable storage medium.

The foregoing embodiments and other embodiments of the inventions of the present disclosure as well as various features and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

DETAILED DESCRIPTION OF THE PREFERRED EMBODIMENTS

As an improvement upon a prior display of images illustrative of a navigation of an interventional device within an anatomical region, the inventions of the present disclosure are premised on a generation of a plurality of spatial images illustrative of an anatomical region within an image space whereby an optical shape sensed position of a tracking node of an OSS interventional device relative to the image space is determinative of an autonomous selection of one of the spatial images for display and may be further determinative of autonomous display format of the selected spatial image.

To facilitate an understanding of the various inventions of the present disclosure, the following description of FIGS. 1A-3B describes exemplary embodiments of an OSS interventional device. From the description of FIGS. 1A-3B, those having ordinary skill in the art will appreciate how to practice numerous and various embodiments of an OSS interventional device.

Figure 1A:
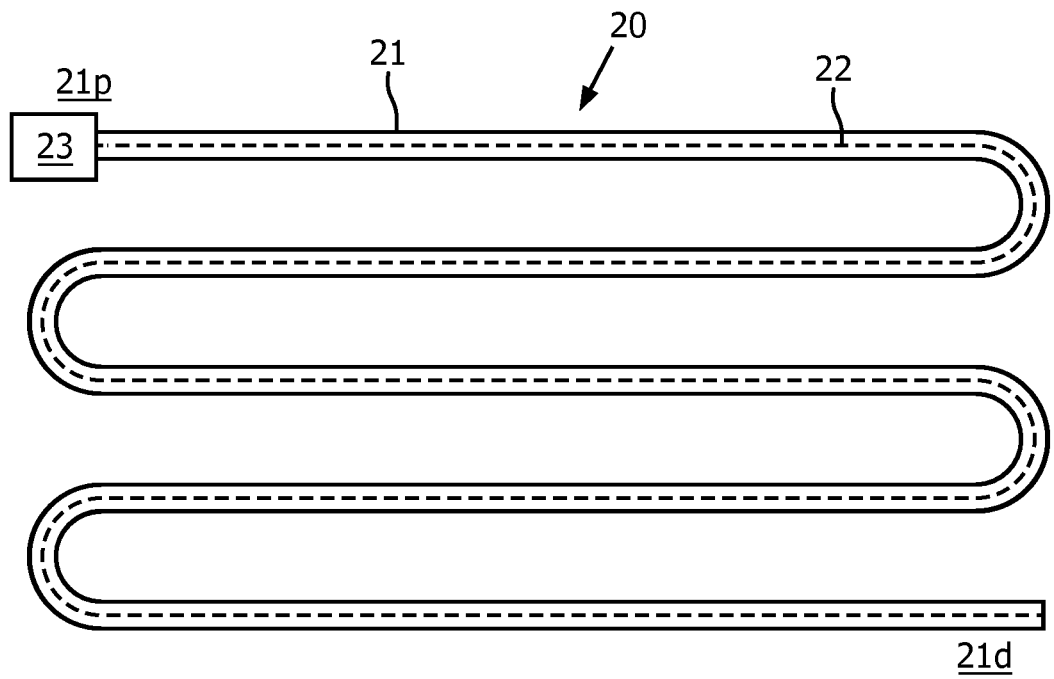
FIGS. 1A-1C illustrates exemplary embodiments of an optical shape sensor as known in the art of the present disclosure.
Figure 1B:
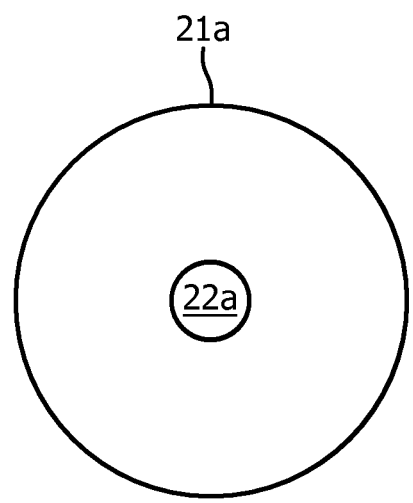
Figure 1C:
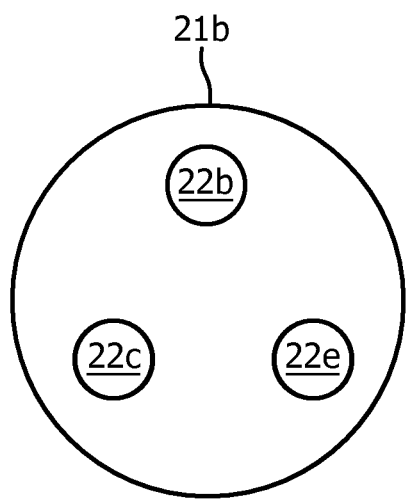

Referring to FIG. 1A, an optical shape sensor 20 applicable to the inventions of the present disclosure includes an optical fiber 21 as a single core optical fiber (e.g., a an optical fiber 21a having a single core 22 as shown in FIG. 1B) or a multi-core optical fiber (e.g. a multi-core optical fiber 21b having multi-cores 22b, 22c and 22d as shown in FIG. 1C). A core of optical fiber 21 has controlled grating patterns (e.g., Fiber Bragg Gratings), a characteristic backscatter (e.g., Rayleigh backscatter) or any other arrangement of reflective elements and/or transmissive elements embedded, etched, imprinted, or otherwise formed in optical fiber 21. In practice, OSS nodes in the form of controlled gratings, characteristic backscatter, or reflective/transmissive elements may extend along any segment or an entirety of optical fiber 21 as symbolically shown by dashed line extending from a proximal end 21p (or guidewire proximal end 31p in FIGS. 3A and 3B) to a distal end 21d (or guidewire distal end 31d in FIGS. 3A and 3B). Also in practice, optical shape sensor 20 may include two (2) or more individual optical fibers 31 that may or may not be helixed.

In practice, optical fiber 21 of optical shape sensor 20 may be made partially or entirely of any glass, silica, phosphate glass or other glasses, or made of glass and plastic or plastic, or other materials used for making optical fibers. For impeding any damage to optical shape sensor 20 when introduced into a patient anatomy via manual or robotic insertion, an optical fiber 21 of optical shape sensor 20 may permanently encircled by a protective sleeve as known in the art.

In practice, the protective sleeve may be made from any flexible material of a specified hardness including, but not limited to, pebax, nitinol, furcation tubing, and stranded metal tubing. Also in practice, the protective sleeve may consist of two or more tubular components of same or different degrees of flexibility and hardness in an overlapping and/or sequential arrangement.

Optical shape sensor 20 may further include an optical connector 23 for connecting optical fiber 21 to another optical fiber, a launch or an optical source (e.g., optical integrator) as will be further described in the present disclosure.

Figure 2:
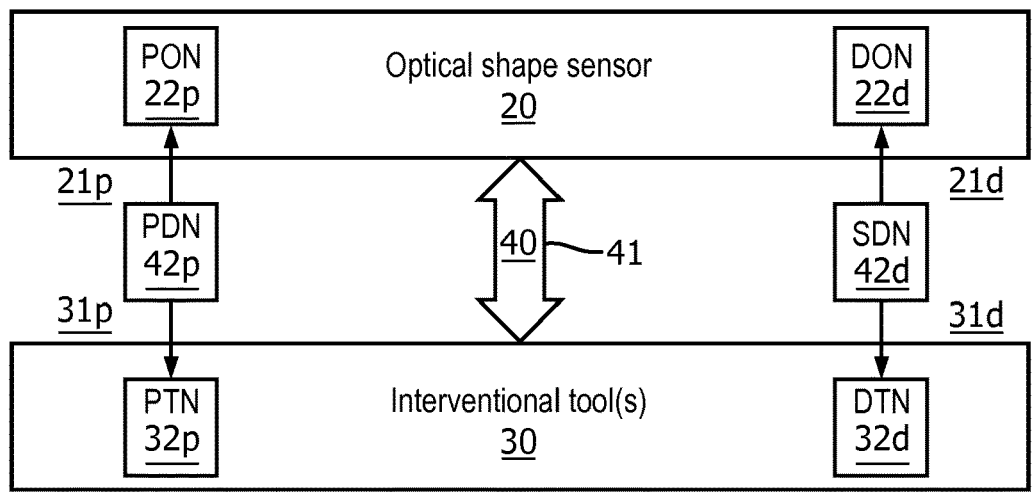
FIG. 2 illustrates an exemplary embodiment of an OSS interventional device as known in the art of the present disclosure.

Referring to FIG. 2, the inventions of the present disclosure provide for an integration 41 of an optical shape sensor 20 and one or more interventional tools 30 to configure an OSS interventional device 40 for an execution of an interventional procedure involving a navigation of OSS interventional device 40 within one or more anatomical regions (e.g., a heart and blood vessels of a cardiovascular system, airways and lungs of a respiratory system, a stomach and intestines of a digestive system, and bores of a musculoskeletal system).

Examples of interventional tool 30 include, but are not limited to, vascular interventional tools (e.g., guidewires, catheters, stents sheaths, balloons, atherectomy catheters, IVUS imaging probes, deployment systems, etc.), endoluminal interventional tools (e.g., endoscopes, bronchoscopes, etc.) and orthopedic interventional tools (e.g., k-wires and screwdrivers).

In practice, an integration of optical shape sensor 20 and interventional tool 30 may be in any configuration suitable for a particular interventional procedure.

Further in practice, a proximal device node 42p of OSS interventional device 40 may be a proximal OSS node 22p of optical shape sensor 20. Alternatively, proximal device node 42p of OSS interventional device 40 may be a proximal tool node 32p mapped to proximal OSS node 22p of optical shape sensor 20 via a mechanical relationship mapping or a shape template based mapping between proximal OSS node 22p and proximal tool node 32p as known in the art of the present disclosure.

Similarly in practice, a distal device node 42d of OSS interventional device 40 may be a distal OSS node 22d of optical shape sensor 20. Alternatively, distal device node 42d of OSS interventional device 40 may be a distal tool node 32d mapped to distal OSS node 22d of optical shape sensor 20 via a mechanical relationship mapping or a shape template based mapping between distal OSS node 22d and distal tool node 32d as known in the art of the present disclosure.

Figure 3A:
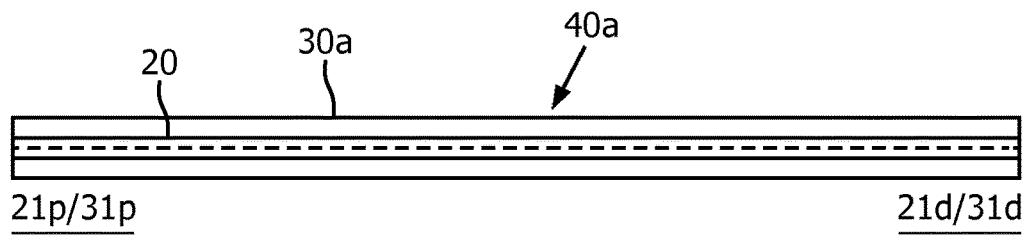
FIGS. 3A and 3B illustrate exemplary embodiments of an integration of a OSS sensor into a guidewire as known in the art of the present disclosure.

For example, FIG. 3A illustrates a optical shape sensor 20 axially embedded within a guidewire 30a to configure an OSS interventional device 40 in the form of a OSS guidewire 40a as known in the art of the present disclosure. OSS guidewire 40a may be incorporated into any interventional procedure involving the utilization of a guidewire whereby the OSS guidewire 40a may be navigated as necessary within anatomical region via a shape reconstruction capabilities of optical shape sensor 20 as known in the art of the present disclosure.

A proximal device node 42p of OSS interventional device 40a may be a proximal OSS node 22p of optical shape sensor 20. Alternatively, proximal device node 42p of OSS interventional device 40a may be a proximal tool node 32p mapped to proximal OSS node 22p of optical shape sensor 20 via a mechanical relationship mapping or a shape template based mapping between proximal OSS node 22p and proximal tool node 32p as known in the art of the present disclosure.

A distal device node 42d of OSS interventional device 40a may be a distal OSS node 22d of optical shape sensor 20. Alternatively, distal device node 42d of OSS interventional device 40a may be a distal tool node 32d mapped to distal OSS node 22d of optical shape sensor 20 via a mechanical relationship mapping or a shape template based mapping between distal OSS node 22d and distal tool node 32d as known in the art of the present disclosure.

Figure 3B:
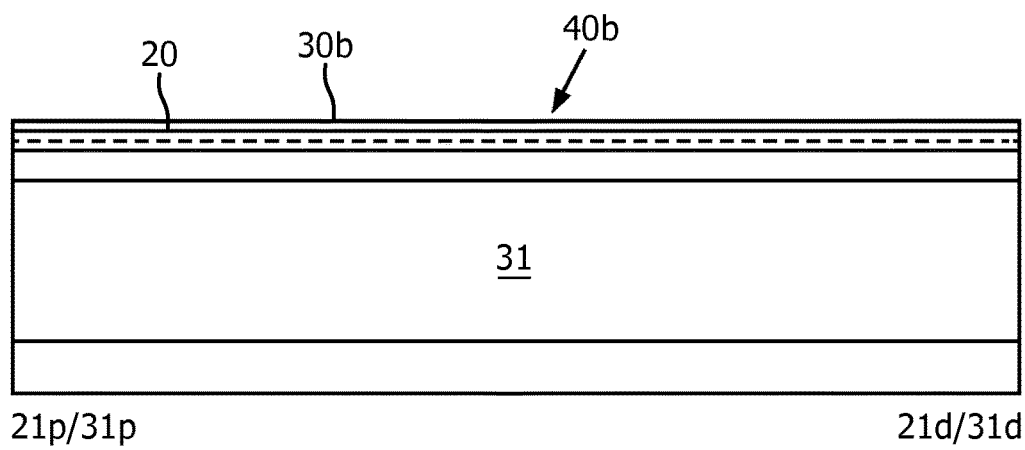

By further example, FIG. 3B illustrates a optical shape sensor 20 as shown or a OSS guidewire 30a may be temporarily or permanently inserted within a channel of a catheter 30b to configure an OSS interventional device 40 in the form of a universal catheter 40b as known in the art of the present disclosure. Universal catheter 40b may be incorporated into any interventional procedure involving the utilization of a working channel 31 of catheter 30b whereby universal catheter 40b may be navigated as necessary within anatomical region(s) via a shape reconstruction capabilities of optical shape sensor 20 as known in the art of the present disclosure.

A proximal device node 42p of OSS interventional device 40b may be a proximal OSS node 22p of optical shape sensor 20. Alternatively, proximal device node 42p of OSS interventional device 40b may be a proximal tool node 32p mapped to proximal OSS node 22p of optical shape sensor 20 via a mechanical relationship mapping or a shape template based mapping between proximal OSS node 22p and proximal tool node 32p as known in the art of the present disclosure.

A distal device node 42d of OSS interventional device 40b may be a distal OSS node 22d of optical shape sensor 20. Alternatively, distal device node 42d of OSS interventional device 40b may be a distal tool node 32d mapped to distal OSS node 22d of optical shape sensor 20 via a mechanical relationship mapping or a shape template based mapping between distal OSS node 22d and distal tool node 32d as known in the art of the present disclosure.

Referring back to FIG. 2, for purposes of the inventions of the present disclosure, a tracking node of OSS interventional device 40 includes any fixed or dynamic point or portion of OSS interventional device 40 between proximal device node 42p and distal device node 42d, or an entirety of OSS interventional device 40.

For example, the tracking node of OSS interventional device 40 may be a distal tip of interventional tool located at distal device node 42d.

By further example, the tracking node of OSS interventional device 40 may be a portion of OSS interventional device 40 between proximal device node 42p and distal device node 42d that is associated with a therapy device (e.g., a balloon or a stent).

By even further example, the tracking node of OSS interventional device 40 may be any portion of OSS interventional device 40 between proximal device node 42p and distal device node 42d that is extending into an anatomical region.

By even further example, the tracking node of OSS interventional device 40 may be any portion of OSS interventional device 40 between proximal device node 42p and distal device node 42d that is positioned in the image space of anatomical region.

Figure 4:
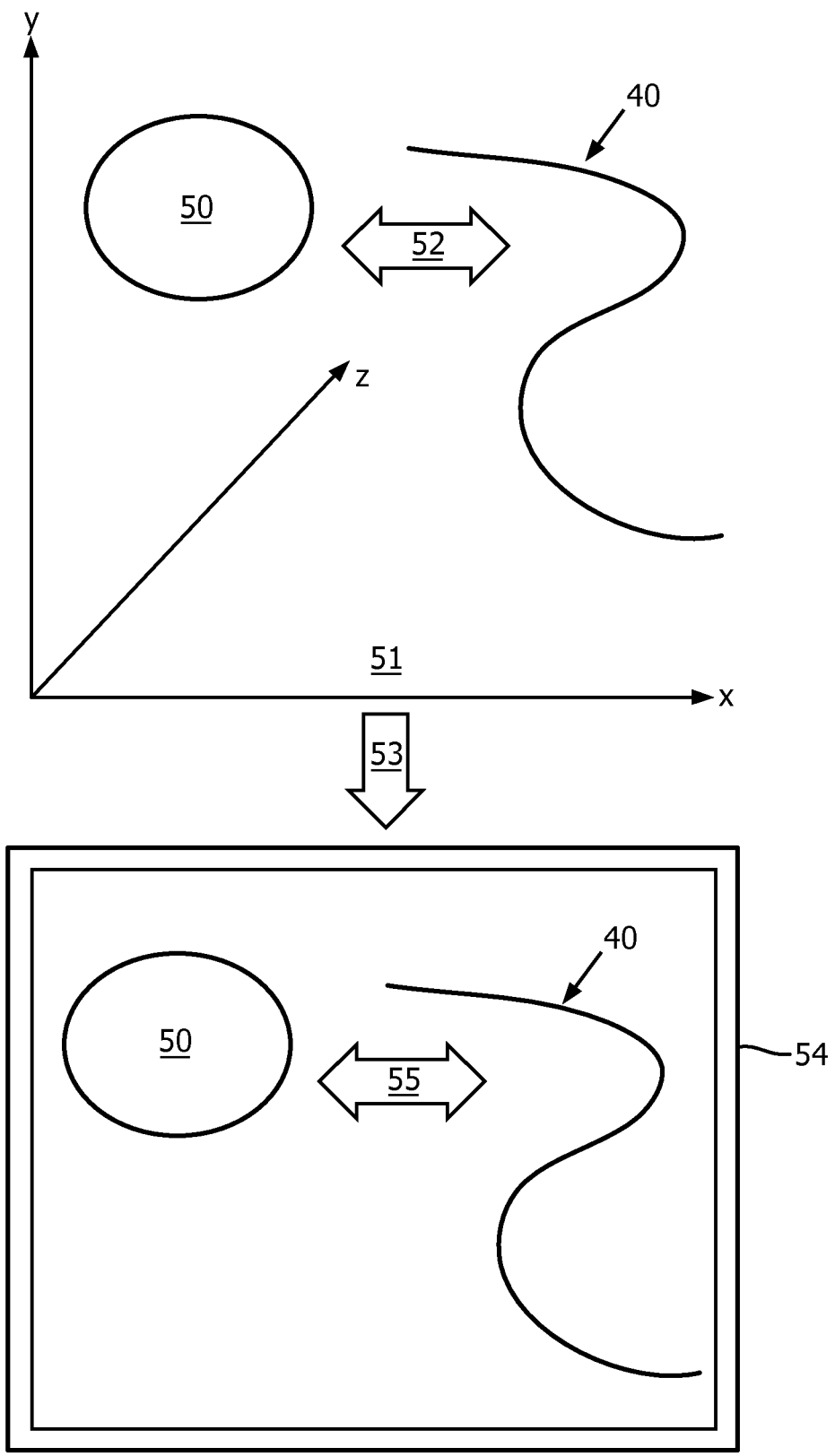
FIG. 4 illustrates an exemplary embodiment of control of a real-time display in accordance with the inventive principles of the present disclosure

Referring to FIG. 4, the inventions of the present disclosure are directed to controlling a real-time display 54 of an animation 53 of a spatial positional relationship 52 between OSS interventional device 40 and an object 50 (e.g., an anatomical feature, a therapy device or an additional OSS interventional device 40) derived from a shape of the optical shape sensor 20 of OSS interventional device 40.

Specifically, interventional device 40 and object 50 are relatively positioned within a space 51 represented by the XYZ coordinate system.

In one embodiment, a minimum distance between the OSS interventional device 40 and the object 50 defines the spatial positional relationship 52 between the OSS interventional device 40 and the object 50 whereby, as will be further described herein, animation 53 includes one of an in-plane indicator of the OSS interventional device 40 being in-plane with an imaging of the object 50, a forward out-of-plane indicator of a forward-facing orientation of the OSS interventional device 40 being out-of-plane with the imaging of the object 50, a backward out-of-plane indicator of a backward-facing orientation of the OSS interventional device 40 being out-of-plane the imaging of the object 50 and a contact indicator of a predictive degree of any contact between the OSS interventional device 40 and the object 50.

In a second embodiment, a clinical alignment between the OSS interventional device 40 and the object 50 defines the spatial positional relationship 52 between the OSS interventional device 40 and the object 50 whereby, as will be further described herein, animation 53 includes one of an inline indicator of the OSS interventional device 40 being aligned with the object 50 in accoardance with an interventional procedure, and an outline indicator of the OSS interventional device 40 being misaligned with the object 50 in accoardance with the interventional procedure.

In a third embodiment, a clinical depth between the OSS interventional device 40 and the object 50 defines the spatial positional relationship between the OSS interventional device 40 and the object 50 whereby, as will be further described herein, animation 53 includes one of an in-depth indicator of the OSS interventional device 40 being within a depth range of the object 50 in accoardance with an interventional procedure, or an out-of-depth indicator of the OSS interventional device 40 being outside of the depth range of the object 50 in accoardance with the interventional procedure.

Figure 5:
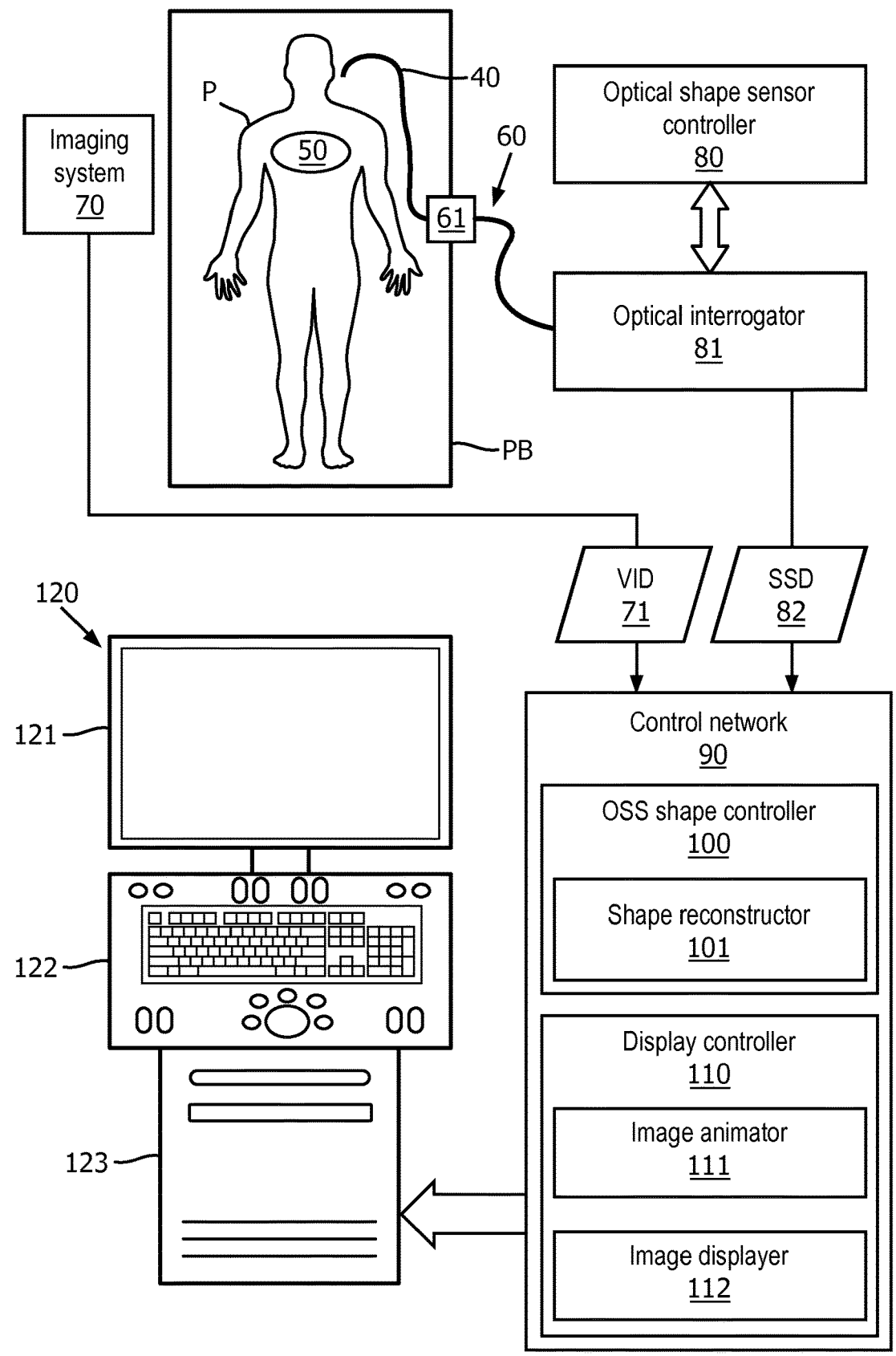
FIG. 5 illustrates an exemplary embodiment of a OSS animated display system in accordance with the inventive principles of the present disclosure.
Figure 6:
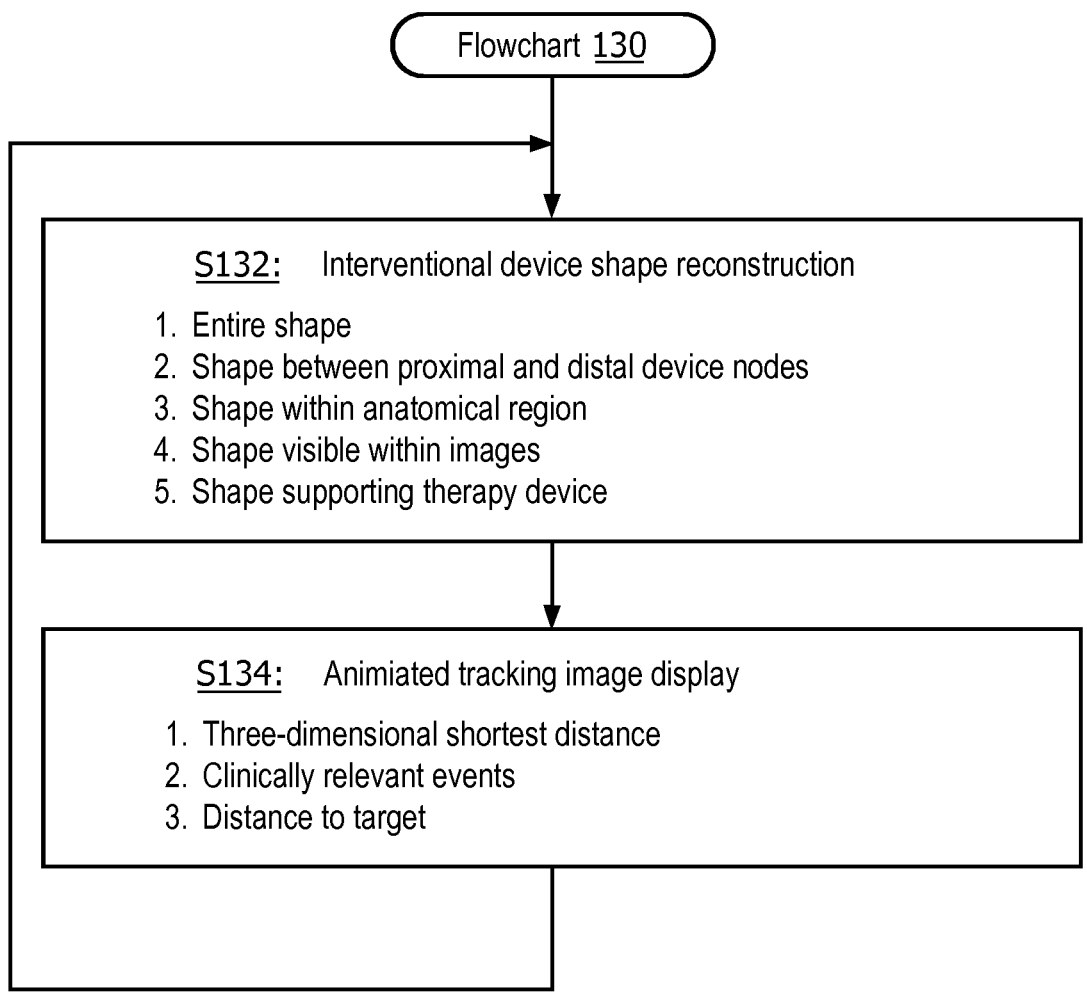
FIG. 6 illustrates an exemplary embodiment of a flowchart representative of an OSS animated display in accordance with the inventive principles of the present disclosure.

To facilitate a further understanding of the inventions of the present disclosure, the following description of FIGS. 5 and 6 describes exemplary embodiments of an OSS animated display system and method incorporating the inventive principles of the present disclosure. From the description of FIGS. 5 and 6, those having ordinary skill in the art will appreciate how to apply the inventive principles of the present disclosure to practice numerous and various embodiments of an OSS animated display system and method incorporating the inventive principles of the present disclosure.

Referring to FIG. 5, an OSS animated display system of the present disclosure employs an OSS interventional device 40 (FIG. 2), an imaging system 70 and a control network 90 including a OSS shape controller 100 and a display controller 110 installed on a workstation 120. The OSS interventional system provides an automatic update of a real-time display by workstation 120 of images illustrative of a navigation of the OSS interventional device 40 within an anatomical region of a patient P based on an optically shape sensed position (i.e., a location and/or an orientation) of the OSS interventional device 40 within the anatomical region of patient P in accordance with the inventive principles of the present disclosure previously described in the present disclosure in connection with FIG. 4.

In practice, OSS interventional device 40 includes an integration of an optical shape sensor 20 and one or more interventional tool(s) 40 as previously described in the present disclosure in connection with FIGS. 1A-3B. For example, OSS interventional device 40 may be OSS guidewire 40*a* (FIG. 3A) or universal catheter 40*b* (FIG. 3A).

In practice, imaging system 70 may implement any type of imaging modality for generating a volume image(s) of anatomical region(s) of patient P (e.g., an X-ray system, a MRI system, a CT system, an ultrasound system, etc.).

In practice, OSS shape controller 100 and display controller 110 may embody any arrangement of hardware, software, firmware and/or electronic circuitry for an automatic update of a real-time display by workstation 120 of images illustrative of a navigation of the OSS interventional device 40 within the anatomical region of patient P in accordance with the inventive principles of the present disclosure.

In one embodiment, OSS shape controller 100 and display controller 110 may include a processor, a memory, a user interface, a network interface, and a storage interconnected via one or more system buses.

The processor may be any hardware device, as known in the art of the present disclosure or hereinafter conceived, capable of executing instructions stored in memory or storage or otherwise processing data. In a non-limiting example, the processor may include a microprocessor, field programmable gate array (FPGA), application-specific integrated circuit (ASIC), or other similar devices.

The memory may include various memories, as known in the art of the present disclosure or hereinafter conceived, including, but not limited to, L1, L2, or L3 cache or system memory. In a non-limiting example, the memory may include static random access memory (SRAM), dynamic RAM (DRAM), flash memory, read only memory (ROM), or other similar memory devices.

The operator interface may include one or more devices, as known in the art of the present disclosure or hereinafter conceived, for enabling communication with a user such as an administrator. In a non-limiting example, the operator interface may include a command line interface or graphical user interface that may be presented to a remote terminal via the network interface.

The network interface may include one or more devices, as known in the art of the present disclosure or hereinafter conceived, for enabling communication with other hardware devices. In a non-limiting example, the network interface may include a network interface card (NIC) configured to communicate according to the Ethernet protocol. Additionally, the network interface may implement a TCP/IP stack for communication according to the TCP/IP protocols. Various alternative or additional hardware or configurations for the network interface will be apparent\

The storage may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage may store instructions for execution by the processor or data upon with the processor may operate. For example, the storage may store a base operating system for controlling various basic operations of the hardware. The storage may further store one or more application modules in the form of executable software/firmware.

More particularly, still referring to FIG. 5, an application module of OSS shape controller 100 is a shape reconstructor 101 for reconstructing a portion or an entirety of a shape of OSS interventional device 40 in response to shape sensing data 82 as known in the art of the present disclosure and further exemplary described in the present disclosure.

Further, application modules of display controller 110 include an image animator 111 for autonomously selecting tracking image among a plurality of spatial images in accordance with the inventive principles of the present disclosure as will be further exemplarily described in the present disclosure, and an image displayer 112 for controlling a display of the selected tracking image in accordance with the inventive principles of the present disclosure as will be further exemplarily described in the present disclosure.

Still referring to FIG. 5, workstation 120 includes a known arrangement of a monitor 121, a keyboard 122 and a computer 123.

In practice, control network 90 may be alternatively or concurrently installed on other types of processing devices including, but not limited to, a tablet or a server accessible by workstations and tablets, or may be distributed across a network supporting an execution of interventional procedures involving OSS interventional device 40.

Also in practice, OSS shape controller 100 and display controller 110 may be integrated components, segregated components or logically partitioned components of control network 90.

Still referring to FIG. 5, in operation, imaging system 70 pre-operatively and/or intra-operatively generates volume image data 71 for displaying a volume image of the subject anatomical region(s) of patient P. Volume image data 71 is communicated to control network 90 (e.g., a streaming or an uploading of volume image data 71) whereby image displayer 112 may control an overlay display of a reconstructed shape of OSS interventional device 40 on the volume image of anatomical region(s) of patient P as known in the art of the present disclosure. For example, monitor 121 may display on overlay of a reconstructed shape of OSS interventional device 40 on a volume image of a vascular structure of patient P.

OSS interventional device 40 distally extends from a launch 61 adjoined to a rail of patient bed PB as shown, or alternatively adjoined to a cart (not shown) next to patient bed PB or alternatively adjoined to a workstation (e.g., workstation 100 or a tablet (not shown)). An optical fiber 60 proximally extends from launch 61 to an optical integrator 81. In practice, optical fiber 60 may be a separate optical fiber connected to optical shape sensor 20 of OSS interventional device 40 at launch 61, or a proximal extension of optical shape sensor 20 extending through launch 61.

As known in the art of the present disclosure, a OSS sensor controller 80 controls a cyclical emission of light by optical interrogator 81 via optical fiber 60 into optical shape sensor 20 whereby the light is propagated through optical shape sensor 20 to a distal tip of OSS interventional device 40 to thereby generate shape sensing data 82 informative of a shape of OSS interventional device 40 relative to launch 61 serving as a fixed reference position. In practice, the distal end of optical shape sensor 20 may be closed, particularly for light reflective embodiments of optical shape sensor 20, or may be opened, particularly for light transmissive embodiments of optical shape sensor 20.

Shape sensing data 82 serves as position tracking data whereby OSS sensor controller 80 controls a communication of a temporal frame sequence of shape sensing data 82 to OSS shape controller 100 as known in the art of the present disclosure. More particularly, each frame consists of a single interrogation cycle of the strain sensors of optical shape sensor 20 (e.g., Fiber Bragg Gratings or Rayleigh backscatter) whereby shape reconstructor 101 reconstructs a shape of optical shape sensor 20 on a temporal frame basis as known in the art of the present disclosure, which provides for a reconstruction of a portion or an entirety of the shape of OSS interventional device 40 derived from the particular integration of optical shape sensor 20 and interventional tool(s) 40.

In practice, shape reconstructor 101 may implement any reconstruction technique for reconstructing the portion/entirety of a shape of OSS interventional device 40 as known in the art of the present disclosure.

In one reconstruction embodiment, shape reconstructor 101 executes a delineation of pose of the portion/entirety of a shape of OSS interventional device 40 via shape sensing data 82 on a temporal frame basis within a coordinate system corresponding to optical interrogator 81.

In a second reconstruction embodiment, shape reconstructor 101 executes a registration of a coordinate system of optical interrogator 81 to a coordinate system of imaging system 70 whereby shape reconstructor 101 may position and orientate a delineation of the portion/entirety of a shape of OSS interventional device 40 via shape sensing data 82 on a temporal frame basis within the coordinate system of imaging system 70.

FIG. 6 illustrates a flowchart 130 representative of an OSS animated display method of the present disclosure that is implemented by the OSS animated display system of FIG. 5.

Prior to or during an execution of flowchart 130, the spatial images are individually registered to a three-dimensional (3D) shape of optical shape sensor 20 (FIG. 5) within OSS interventional device 40 by OSS shape controller 100 or display controller 110.

In one embodiment, a 3D shape of optical shape sensor 20 is registered to the image space of the spatial images to thereby generate an individual registration matrix for each spatial image. OSS shape controller 100 may utilize any spatial registration method suitable for the subject medical procedure, including, for example, object feature detection, marker detection, point based registration, or external tracking methods.

Referring to FIGS. 5 and 6, a stage S132 of flowchart 130 encompasses shape reconstructor 101 reconstructing a portion or an entirety of a shape of OSS interventional device 40 in response to shape sensing data 82 as known in the art of the present disclosure.

In one exemplary embodiment, shape reconstructor 101 may reconstruct an entire shape of OSS interventional device 40 between proximal device node 42p and distal device node 42d.

In a second exemplary embodiment, shape reconstructor 101 may reconstruct a portion of OSS interventional device 40 between proximal device node 42p and distal device node 42d.

In a third exemplary embodiment, shape reconstructor 101 may reconstruct a portion of the OSS interventional device 40 between an intermediate device node and a distal device node 42d with intermediate device node being identified as the node at the entry point of an anatomical region AR as known in the art of the present disclosure.

In a fourth exemplary embodiment, shape reconstructor 101 may reconstruct a portion of the OSS interventional device 40 between an intermediate device node and a distal device node 42d with intermediate device node being identified as the node at the entry point of an image space of the registered spatial images.

In a fifth exemplary embodiment, shape reconstructor 101 may reconstruct a portion of the OSS interventional device 40 between a proximal tool node 32p and a distal tool node 32d enclosing a therapy device (e.g., a balloon, a stent, an endograft, etc.).

Referring back to FIGS. 5 and 6, a stage S134 of flowchart 130 encompasses an animated display of a tracking image selected among the registered spatial images. The following is a description of three embodiments of stage S134.

Three-Dimensional (3D) Shortest Distance.

Generally, when registered with imaging system 70 (FIG. 5), an integration of an optical shape sensor 20 into interventional tool 30 to form an OSS interventional device 40 as shown in FIG. 2 provides information from which any computed distance in 3D and real time may be derived, either between multiple OSS interventional devices 40 or between an OSS interventional device 40 and any landmark of interest in the anatomy or image device. Accordingly, the shortest distance in 3D and in real time between OSS interventional device 40 and any other point of interest in the same space (either OSS interventional device 40 or an anatomical landmark) may be computed. This computed distance can be displayed and made available to the operator to guide navigation and/or deployment of OSS interventional device 40 in a safe manner by visualizing the relationship between the location of the OSS interventional device 40 with respect to the anatomy of interest or with respect to another OSS interventional device 40.

Figure 7A:
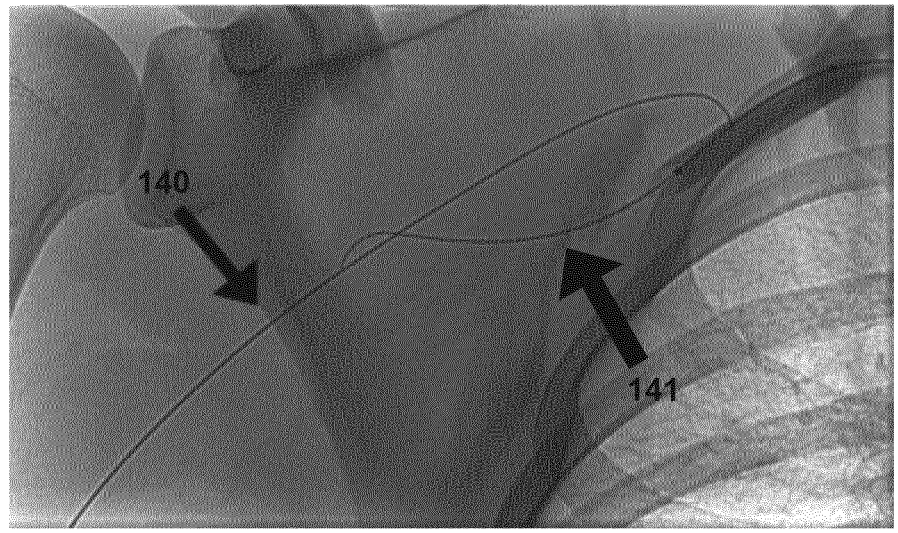
FIGS. 7A-7C illustrate a first exemplary minimum distance animation in accordance with the inventive principles of the present disclosure.
Figure 7B:
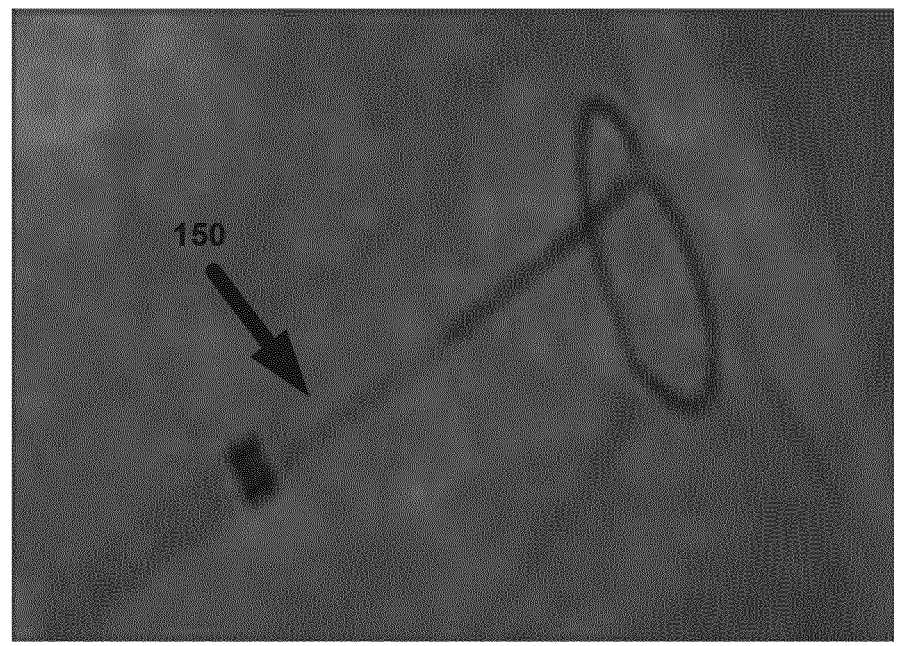
Figure 7C:
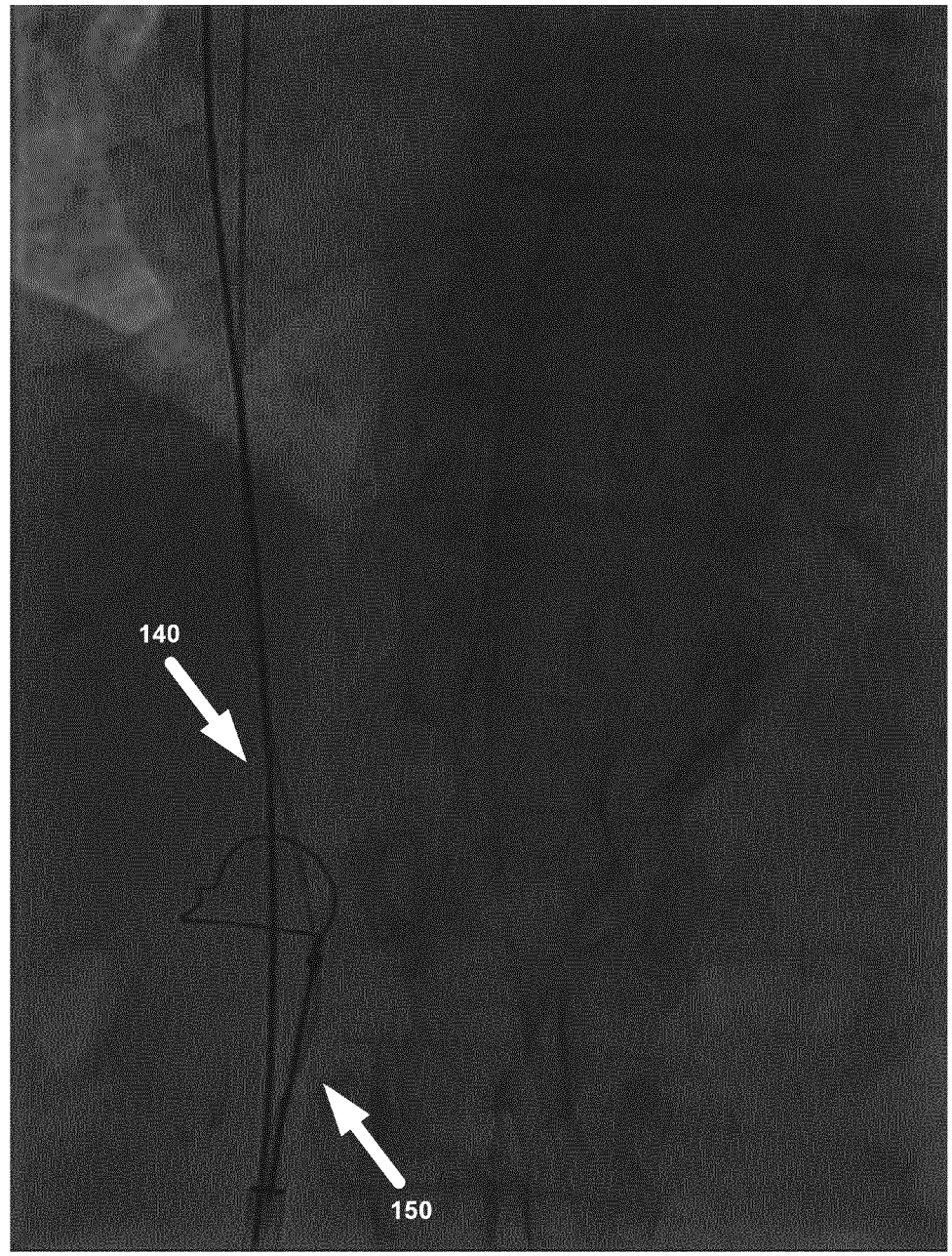

For example, a through-and-through wire technique for an endovascular procedure involving an introduction of a soft 0.035 hydrophilic OSS guidewire 140 from a brachial access through a 6F 10-cm sheath meeting a soft 0.035 hydrophilic guidewire 141 from transfemoral access as shown in FIG. 7A. An 15- to 20-mm OSS ensnare (endovascular snare system) is transbrachially introduced, and the transfemoral wire is snared and externalized through the brachial access. An example of an OSS ensnare 150 as imaged under X ray as shown in FIG. 7B, and FIG. 7C shows a snaring action of OSS guidewire 140 which benefits from a 3D shortest distance computation as further described in the present disclosure. After establishing this brachial-femoral through-and-through wire, the placement of stent grafts through tortuous aortic anatomy becomes feasible. A through-and-through wire technique can be applied also by snaring the transbrachial guidewire by introducing a snare from trans-femoral access, or to place guidewires in other anatomical areas as well, as for instance by snaring a transfemoral guidewire over the aortic bifurcation (cross over) from the left common iliac artery into the right common iliac artery. Many variations of this technique currently exist, such as the double-wire technique, which has been successfully applied to cerebral aneurysm repair.

Additional cases applicable for 3D shortest distance computation of the present disclosure include, but are not limited to, (1) bringing retrograde and antegrade wires to meet during CTO crossing, (2) cannulation of the contralateral gate during abdominal aneurysm repair, (3) navigation of a device to a specific anatomical target (e.g. navigation of a transseptal needal to a landmark placed by the operator), and (4) navigation of a device to a position on another medical device (e.g. cannulation through a FEVAR graft to the left renal).

More particular to a relationship between an OSS interventional device 40 of the present disclosure and anatomy, for endovascular procedures, the interplay between an OSS interventional device 40 and anatomy is key to the deployment of the therapy as planned. Generally, the relationship between an OSS interventional device 40 and anatomy and anatomy can be classified under two different groups.

For embodiments of the first group, the OSS interventional device 40 and anatomy should avoid contact with the vascular tissue, and, most importantly, with thrombi, calcifications, artheriosclerotic plaques. Next to visualizing an OSS interventional device 40 and anatomy in 3D in real time, a minimal 3D distance of the an OSS interventional device 40 and anatomy, or part of it, from anatomical landmarks of interest, for instance calcifications, severely stenotic regions, thrombi, as given in a 3D anatomical image dataset, in order to warn the user and guide the deployment of the OSS interventional device 40 and anatomy inside the vasculature more safely and in a more effective way. The computed minimal distance may be given in real time and the critically close location on OSS interventional device 40 may be displayed with respect to the anatomical element of interest.

Figure 8:
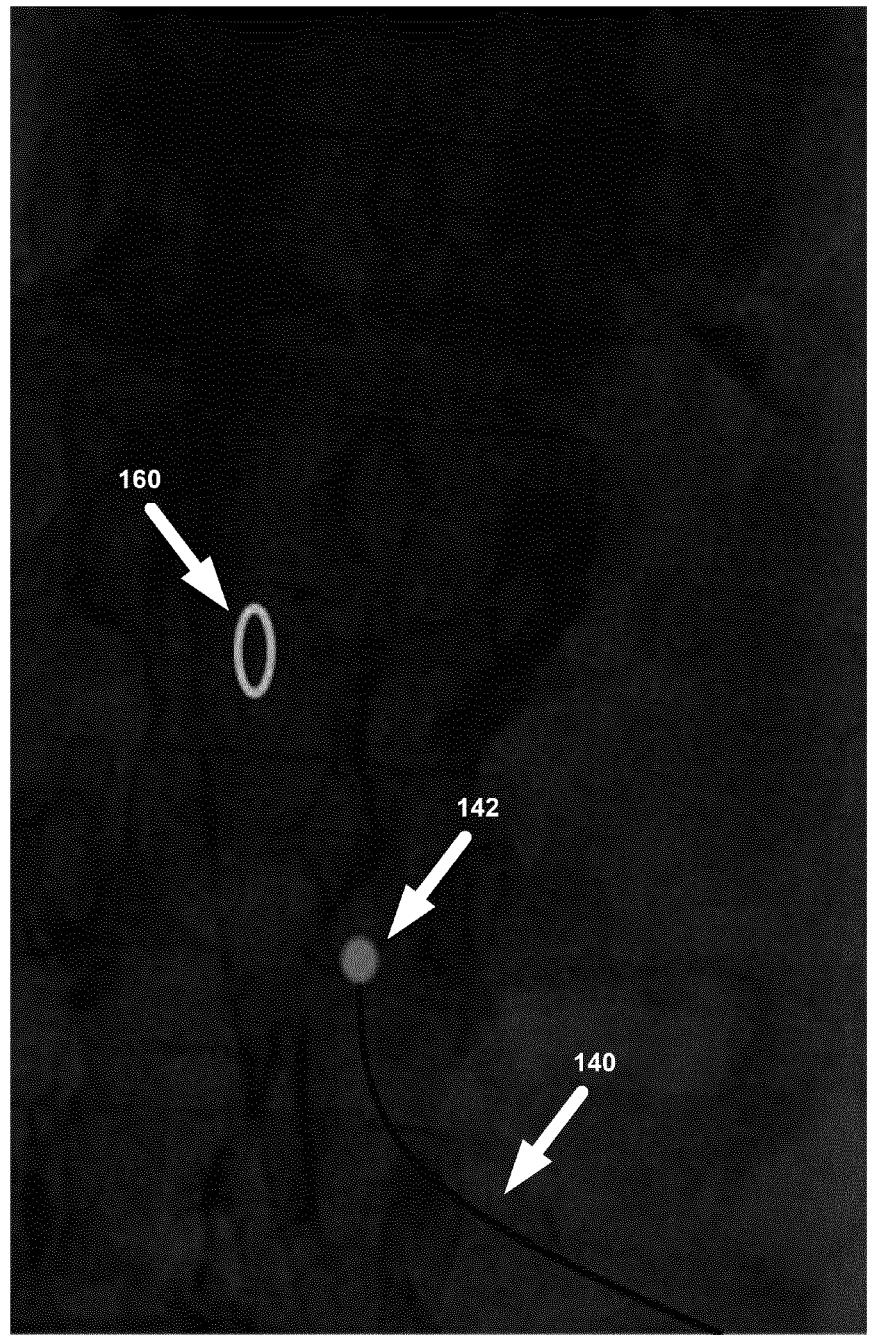
FIG. 8 illustrates a second exemplary minimum distance animation in accordance with the inventive principles of the present disclosure.

For the embodiments of the second group, the goal of the endovascular technique is to navigate the OSS interventional device 40 towards a specific anatomical landmark and/or region of interest. In this case, the minimal 3D distance of the OSS interventional device 40, or part of it, from the anatomical landmark of interest is computed. The anatomical landmark would be given either by a 3D CTA dataset or a 3D intraprocedural CT (Cone Beam CT, 3D rotational angiography), which have been co-registered with OSS interventional device 40. Again, the distance may be displayed in real time, along with the location of the instrument, which is closest to the anatomical landmark of interest. In a two-dimesnional (2D) display of the scene, an indicator (color, size, halo) can also indicate if the OSS interventional device 40 is in-plane with the target or out of plane (near and far being represented differently). FIG. 8 shows an example of the OSS interventional device 40 approaching a landmark 160 where a halo 142 at the tip of the OSS interventional device 140 indicates green when in-plane, red when it is out of plane towards the viewer and blue when it is out of plane away from the viewer.

More particular to a relationship between an OSS interventional device 40 of the present disclosure and a vascular therapy device (e.g., an endograft or a stent) or specific parts of it, may be critical to the technical success of an endovascular procedure. In this case, a computed shortest distance between OSS interventional device 40, or part of it, and the vascular therapy device, or part of it, as given by a 3D image dataset (either a pre-operative 3D CT or a intraoperative Cone Beam CT or 3D rotational angiography), enhance guidance for the operator, either to cannulate the stent graft (or part of it) or to avoid coming too close to it. In case the therapy device is being tracked an OSS interventional device 40 as well, the shortest distance in 3D may be computed and displayed in real time between an OSS interventional device 40, or part of it, and an OSS representation of the vascular therapy device, or part of it.

More particular to a relationship between an OSS interventional device 40 of the present disclosure and planar imaging of an anatomy, a shortest distance onto one plane is useful when the anatomical information is only known on one plane. In this embodiment, the shortest distance between an OSS interventional device 40, or part of it, as projected on that plane, and an anatomical element of interest (as imaged by fluoroscopy on that plane) may be computed in real time. In a bioplane embodiment, a shortest distance between the OSS interventional device 40, or part of it, and an anatomical element, as imaged by X ray, either with fluoroscopy (with biplane system) or with DSAs from two different C-arm orientations, may be computed on two planes in real time.

Figure 9:
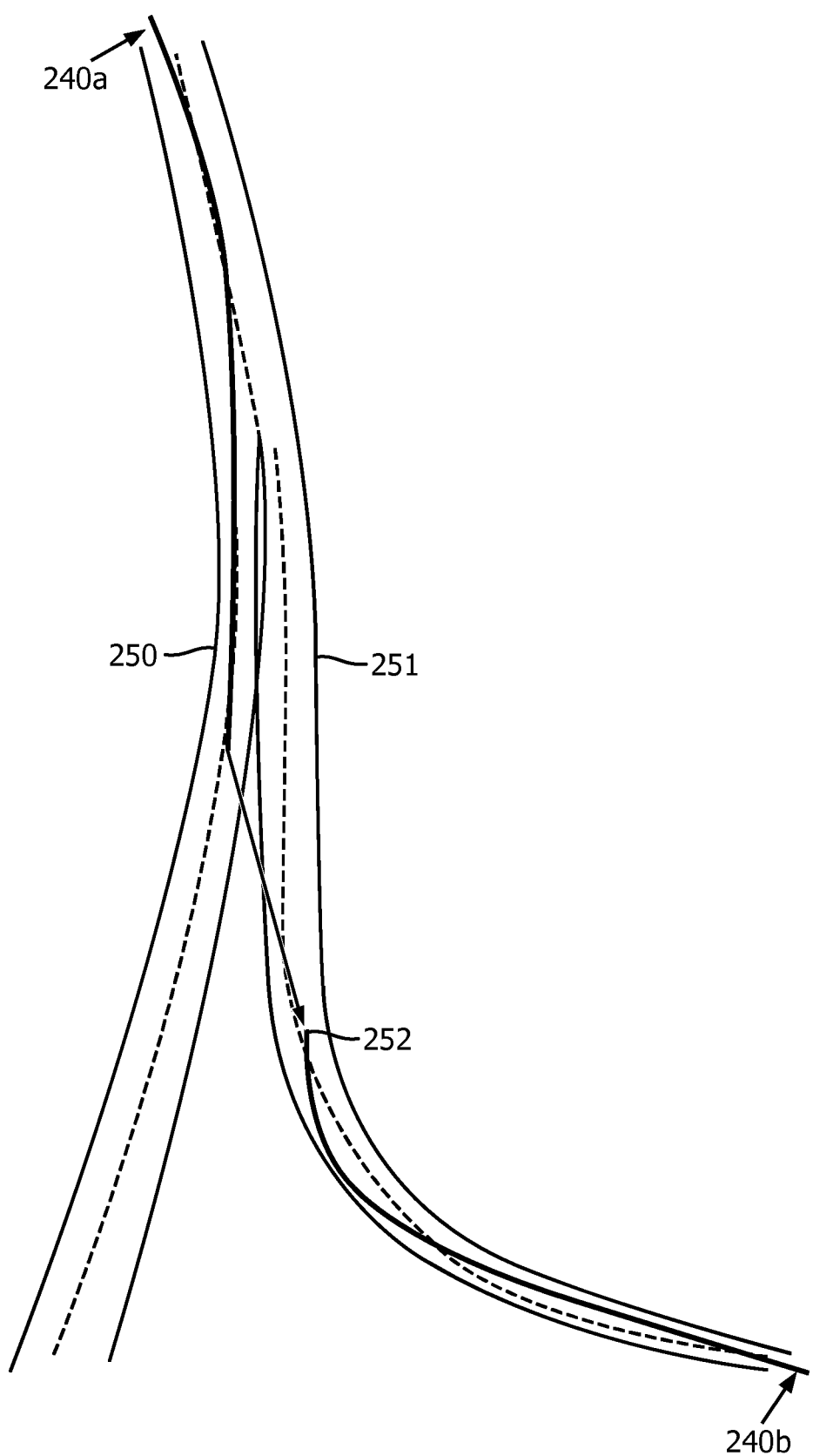
FIG. 9 illustrates a third exemplary minimum distance animation in accordance with the inventive principles of the present disclosure.

More particular to a relationship between an OSS interventional device 40 of the present disclosure and an anatomy or an additional OSS interventional device 40, it may be relevant to know if the position of an OSS interventional device 40 is likely to meet the target antomical element or additional OSS interventional device 40. If there is a 3D model of the anatomy, this information can be incorporated with the two positions to predict if they are likely to meet. This is most relevant in the case of antegrate+retrograde CTO crossing where it can be hard to navigate both an OSS interventional devices 40 to the same vessel. Centerlines from the 3D model of the anatomy may be extracted. In addition, a vector between the two an OSS interventional devices 40 may be computed. If the vector crosses between unique centerlines then the confidence of the two an OSS interventional device 40 meeting can be predicted to be low. FIG. 9 shows an example of an OSS interventional device 240*b* with a vessel 251 trying to meet an OSS interventional device 240*a* with a vessel 250. A vector 252 crosses between unique centerlines of vessels 250 and 251, thus confidencs of the two an OSS interventional devices 240 meeting may be predicted to be low.

Clinical Relevant Events.

Balloon catheters, endografts, and stents are vascular therapy devices frequently used to treat vascular diseases such as atherosclerosis, stenosis, and aneurysms. During cardiovascular interventions, it is necessary to position multiple devices with respect to each other, with respect to anatomical targets, and to monitor the deployment of treatment mechanisms. In practice, clinicians perform positioning and monitoring tasks under fluoroscopic guidance. Display controller 110 (FIG. 5) of the present disclosure visually enhances device activity in real time and in a context relevant manner. In particular, a virtual representation of an OSS interventional device 40 are visually enhanced and/or animated in line to denote clinically relevant events in the context of the intervention. An exemplary scenario is a cannulation of a fenestrated endograft using an OSS interventional device (e.g., OSS guidewire 40a (FIG. 3A) or OSS catheter 40b (FIG. 3B)). When the OSS interventional device is aligned with the fenestration, digital elements representing the fenestration light up, indicating that the OSS interventional device is ready to be advanced through the fenestration.

Figure 10A:
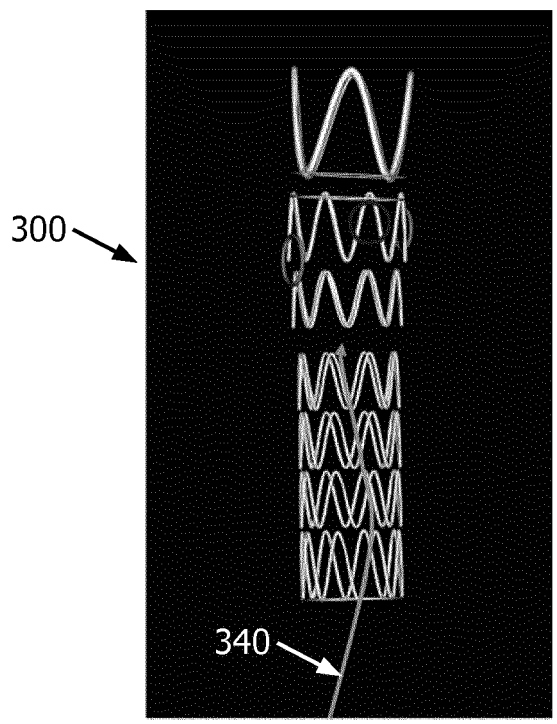
FIGS. 10A-10C illustrate a first exemplary clinical alignment animation in accordance with the inventive principles of the present disclosure.
Figure 10B:
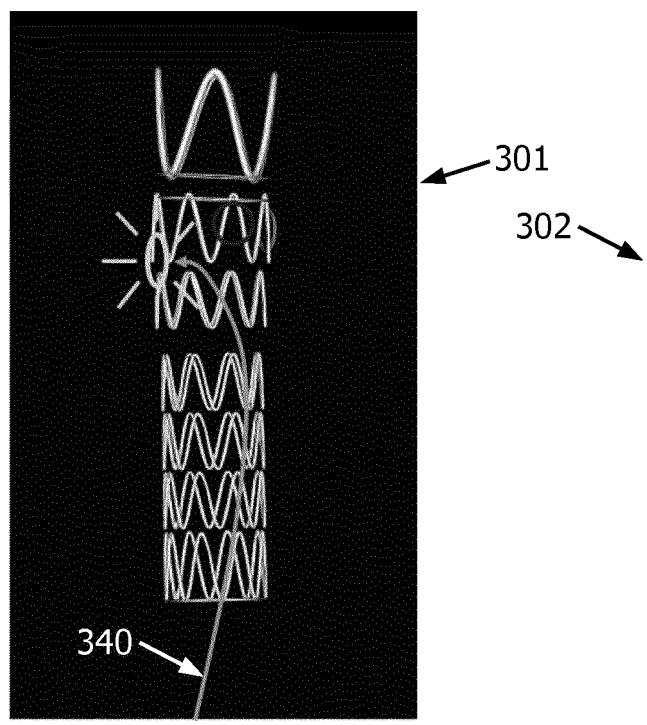
Figure 10C:
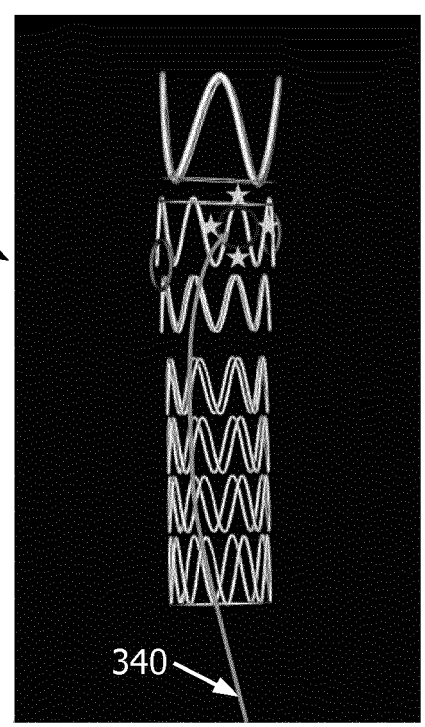

More particularly, an OSS interventional device 340 is not near any fenestration as shown in a virtual representation 300 of FIG. 10A, so rings retain their default colors of green or blue. FIG. 10B shows a virtual representation 301 of OSS interventional device 340 in position to cannulate the left ring, which lights up in yellow to indicate the readiness to advance through the fenestration, and FIG. 10C shows an alternative virtual representation 302 of OSS interventional device 340 in position to cannulate the left ring, which flashes to indicate the readiness to advance through the fenestration. Conversely, the fenestration lighting dims when the OSS interventional device 340 points away. These visual aids ease the cognitive burden of determining the relative positions and orientations of OSS interventional device 340 with respect to each other. This can help overcome the visualization and localization challenges of performing such tasks using a 2D projection as guidance, potentially improving workflow, increasing productivity, and reducing radiation and costs.

Figure 11A:
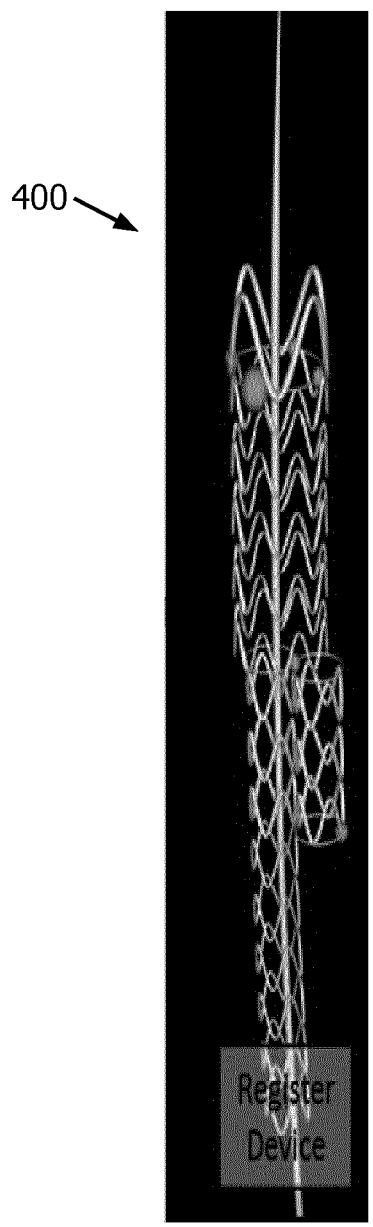
FIGS. 11A-11D illustrate a second exemplary clinical alignment animation in accordance with the inventive principles of the present disclosure.
Figure 11B:
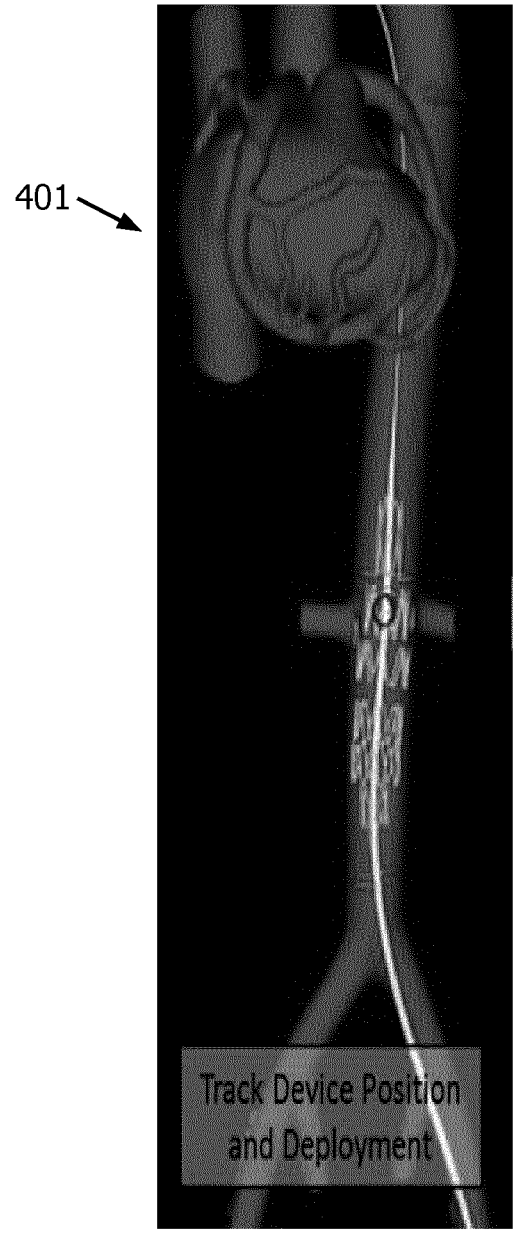
Figure 11C:
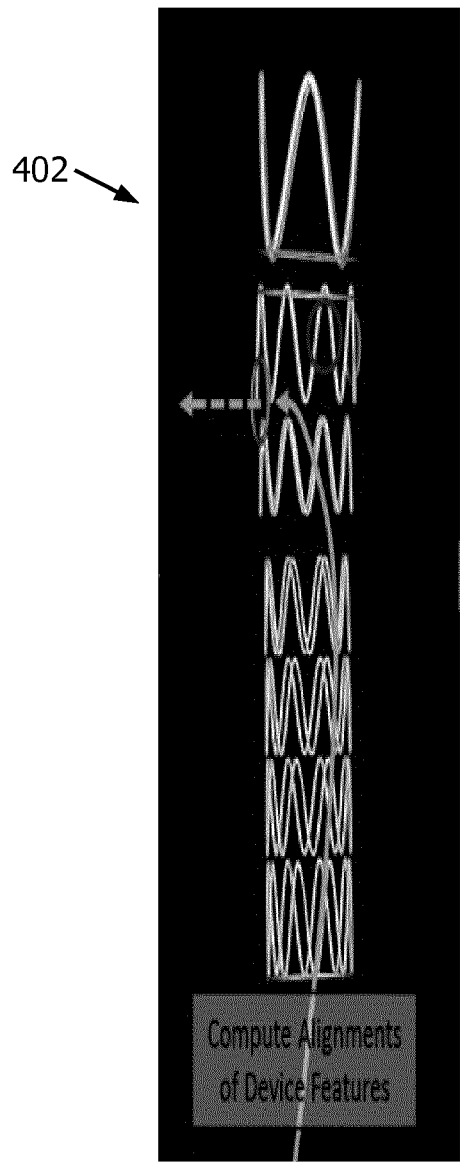
Figure 11D:
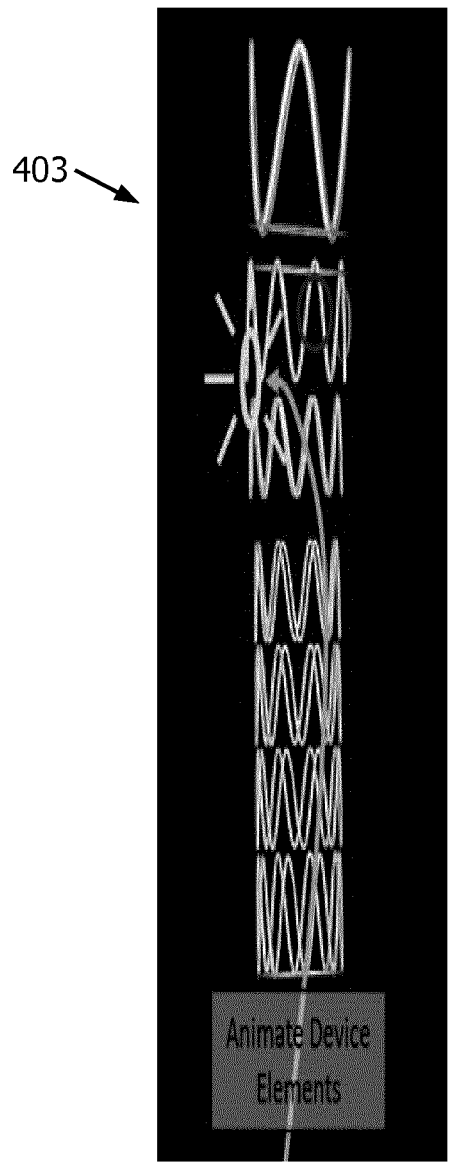

In practice, display controller 110 controls a display of virtual device animations inline to highlight clinically significant activity. To this end, image animator 111 executes a registration of virtual device representations to a correct absolute position on OSS interventional device 40 of the present disclosure as exemplary shown via a virtual representation 400 of FIG. 11A, a tracking of the position of the OSS interventional device 40 and other physical devices (e.g., a vascular therapy device) to determine their spatial relation to each other and a tracking of a deployment of the physical device to fully determine the configuration of device features as exemplary shown via a virtual representation 401 in FIG. 11B, a computation of an alignment of pertinent device features, e.g. the trajectory of the catheter tip and the fenestration on the graft) as exemplary shown via a virtual representation 402 in FIG. 11C and an animation of a virtual device element based on the computed alignment as exemplary shown via a virtual representation 403 in FIG. 11D.

In one embodiment, image animator 111 monitors the alignment of tracked devices, such as an endograft and a catheter, then animating one or more of the devices based on alignment or coincidence of key features.

Figure 12:
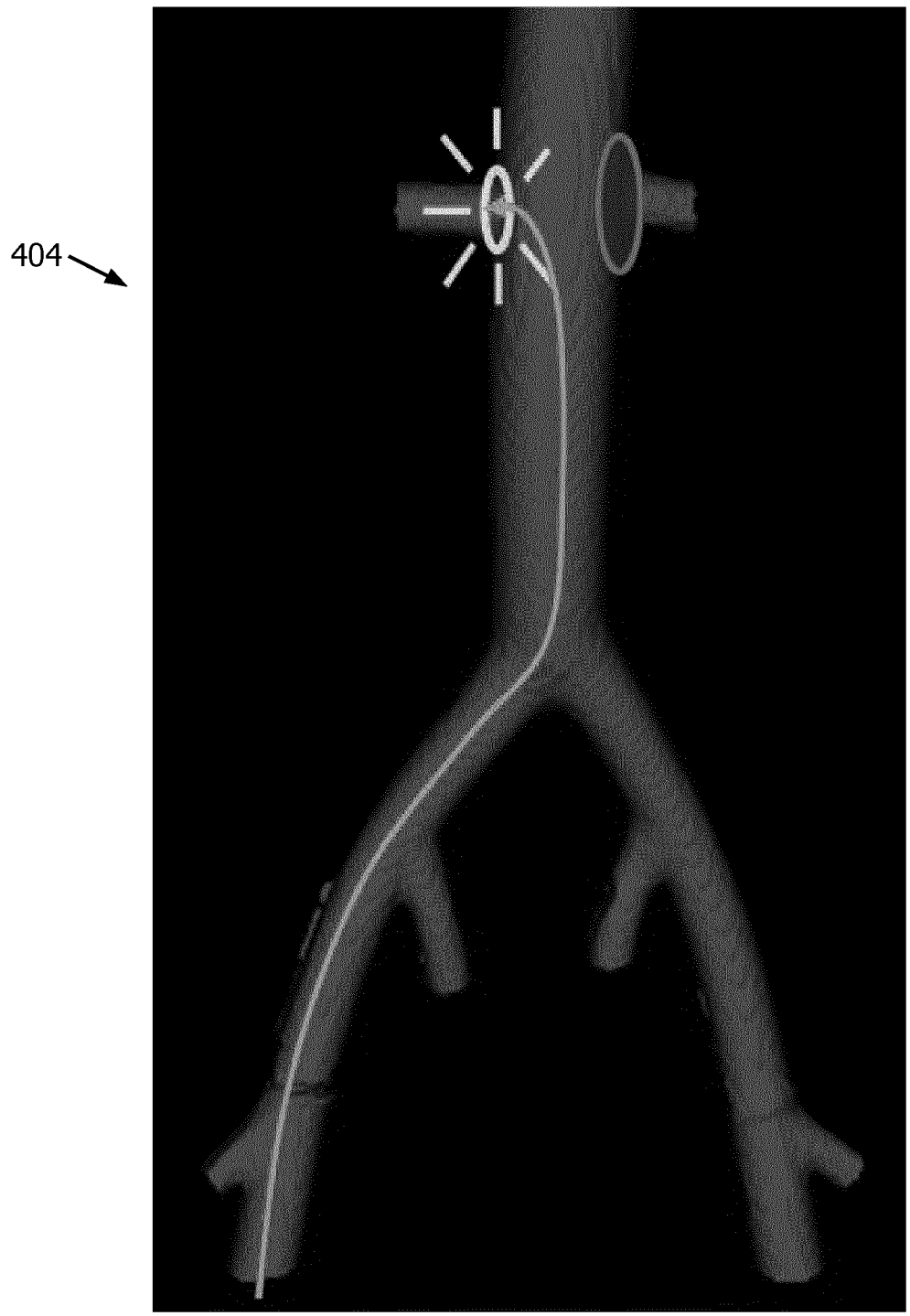
FIG. 12 illustrates a third exemplary clinical alignment animation in accordance with the inventive principles of the present disclosure.

In a second embodiment, image animator 111 monitors the alignment of a tracked device and anatomical targets. The embodiment similar to the previous embodiment, but instead of fenestration markers on a graft, virtual markers are placed on a medical image to reference anatomical targets such as vessel branches. These anatomical markers may or may not be tracked, depending on whether the medical image is intraoperative (e.g., X-ray, ultrasound) or preoperative (e.g., a CT scan). FIG. 12 shows an exemplary virtual representation 404 of an anatomical reference image with anatomical markers overlaid to indicate branches from the abdominal aorta to the renal arteries. These markers may be placed intraoperatively or preoperatively, manually or automatically.

When the OSS interventional device (cyan) points into a vessel opening, the marker corresponding to that opening lights up. This is in comparison to the dull green marker corresponding to the non-pertinent vessel opening. The animation or highlighting may take alternative forms as previously discussed in the present disclosure.

The examples above demonstrate binary on/off illumination of device features, but other variants are possible as well. For example, lighting of the features can increase in brightness with the corresponding device alignment. Alternatively, the portions of the device features closer to the device coincidence can be animated while the features further from the coincidence remain dim. Finally, the animation may take the form of subtle size or shape distortions. For example, the ring in 12 may be enlarged or pulsate in size as the catheter points into the opening, or it can turn into a diamond shape, or any distortion that indicates a clinical event without creating confusion for the clinician.

In another embodiment, virtual device animation may be incorporated into non-compliant balloon inflation as well. More particularly, as known in the art of the present disclosure, animation for non-compliant balloon inflation included size changes to indicate balloon expansion, color changes to indicate balloon pressurization, and blinking to indicate balloon rupture. Additional parameters of clinical interest include balloon under/oversizing and point of opposition against the vessel to be treated.

More particularly, balloon oversizing occurs when the diameter of the balloon catheter is too large for the vessel, which can occur, for example, if the vessel diameter was underestimated due to a misleading fluoroscopic projection. Oversizing is a concern because it may cause excessive trauma to the vessel, including dissection. Upon detection of oversizing, animation of the balloon can take a variety of forms, including blinking on/off, blinking between different colors, overlaying a pattern such as stripes, overlaying indicative markings such as arrows, and so forth. The advantage in each case is that an oversizing alert is shown in-line where the clinician is visually focused, reducing the possibility that the alert is missed. Interpretation of the condition is intuitive—the clinician will not think the balloon is changing colors, for example, and will recognize the clinical event.

Undersizing and correct sizing may be similarly animated. Alternatively, under/correct/oversizing information can be communicated under a unified animation scheme, such as a gradual color change from green to red with green representing a freely inflating balloon, red representing an undersized balloon, and an intermediate color normal apposition of the balloon against the vessel.

Distance to Target.

For this embodiment, visualization is achieved by an encoding of the relative depth a relative depth between an OSS interventional device 40 (FIG. 2) and target by a choice of colors, such as, color orange of the target when a tip of the OSS interventional device 40 is too close, color blue of the target when the tip of the OSS interventional device 40 is too far, and color green of the target when the tip of the OSS interventional device 40 and target are aligned. Further, the color coding could help to have "crisps" transitions between acceptable and unacceptable relative depths. The feeling of depth could furthermore be increased by additional visualization techniques, such as size change, blurring and transparency, which would have more "soft" transitions than color.

In practice, the relative depth between two objects is computed in 3D from a registered position of the OSS interventional device 40 in an imaging space. For example depth of an anatomical target could be computed as the distance from that anatomical target to the X-ray source, or otherwise from the point of view of the projection. Relative depth between the OSS interventional device 40 and the anatomical landmark would be the difference between their depths in the imaging space.

The easiest way to define a target is using a point, in which case both the interaction to get this point and the computation of the relative depth is well known in the art of the present disclosure. Nonetheless, a target could be defined differently, e.g. as a closed curve. In that case, depending on the need, the color coding could be set to either code the depth difference to the center of the target, or alternatively, whether the depth of the tool lies within the range of the depths of the target, for example by keeping a green color when the tip depth lies with the depth range of the target.

Figure 13:
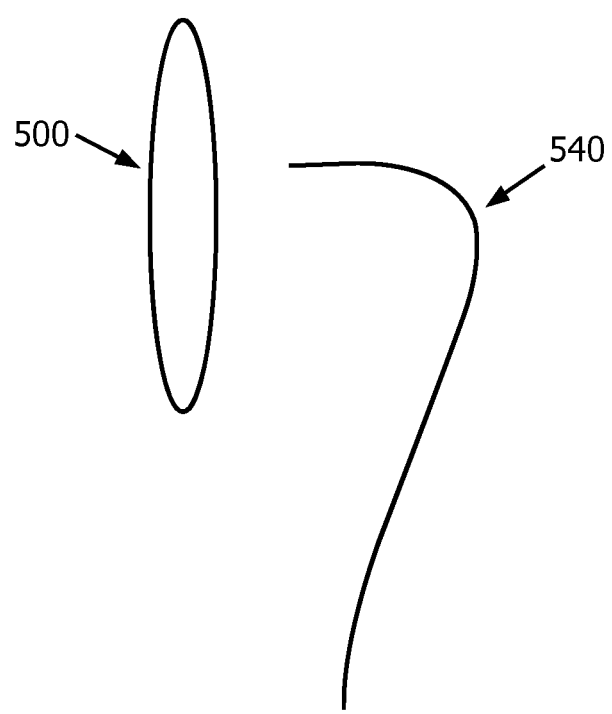
FIG. 13 illustrates an exemplary clinical depth animation in accordance with the inventive principles of the present disclosure.

In FIG. 13, an example of an OSS interventional device 540 navigating towards the fenestration of a graft marker, reconstructed from X-ray and modeled in 3D with an ellipse 500. The ellipse color-code whether the tip of the OSS interventional device 540 lies within its depth range, in which case it could be pushed forward, or whether it lies too near or too far from the fenestration, in which case the interventionist would need to navigate the guide wire accordingly until the ellipse takes the correct color.

Referring back to FIG. 6, stages S132 and S134 are repeated during the interventional procedure to facilitate an optimal viewing of the interventional procedure.

Referring to FIGS. 1-13, those having ordinary skill in the art will appreciate numerous benefits of the present disclosure including, but not limited to, an improvement over prior system, controllers and methods for implementing an interventional procedure by providing an animated display of images illustrative of a navigation of the interventional device within the anatomical region based on optical shape sensing information of a position (i.e., a location and/or an orientation) of the interventional device within the anatomical region.

Furthermore, as one having ordinary skill in the art will appreciate in view of the teachings provided herein, features, elements, components, etc. described in the present disclosure/specification and/or depicted in the Figures may be implemented in various combinations of electronic components/circuitry, hardware, executable software and executable firmware and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the inventive principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present disclosure can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present disclosure and disclosure.

Having described preferred and exemplary embodiments of the inventions of the present disclosure, (which embodiments are intended to be illustrative and not limiting), it is noted that modifications and variations can be made by persons having ordinary skill in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. An optical shape sensing (OSS) animated display system for display of an OSS interventional device, including an integration of at least one optical shape sensor and at least one interventional tool, the OSS animated display system comprising:
- a monitor; and
- a display controller configured to derive an animation indicating a current spatial positional relationship between the OSS interventional device and a previously determined target object during an interventional procedure from a shape of the at least one optical shape sensor, and to control a real-time display on the monitor of a reconstructed shape of the OSS interventional device and the animation indicating the current spatial positional relationship between the OSS interventional device and the target object for tracking position and/or deployment of the OSS interventional device relative to the target object during the interventional procedure.

2. The OSS animated display system of claim 1, wherein the target object is one of an anatomical feature, a therapy device or an additional interventional device.

3. The OSS animated display system of claim 1,
wherein the display controller is further configured to compute a minimum distance between the OSS interventional device and the target object defining the current spatial positional relationship between the OSS interventional device and the target object based on the shape of the at least one optical shape sensor; and
wherein the animation indicating the current spatial positional relationship between the OSS interventional device and the target object comprises an animation indicating the minimum distance between the OSS interventional device and the target object computed by the display controller.

4. The OSS animated display system of claim 3,
wherein the animation indicating the minimum distance between the OSS interventional device and the target object computed by the display controller includes one of:
- an in-plane indicator of the OSS interventional device being in-plane with an imaging of the target object;
- a forward out-of-plane indicator of a forward-facing orientation of the OSS interventional device being out-of-plane with the imaging of the target object;
- a backward out-of-plane indicator of a backward-facing orientation of the OSS interventional device being out-of-plane the imaging of the target object; and
- a contact indicator of a predictive degree of any contact between the OSS interventional device and the target object.

5. The OSS animated display system of claim 1,
wherein the display controller is further configured to compute a clinical alignment between the OSS interventional device and the target object defining the current spatial positional relationship between the OSS interventional device and the object based on the shape of the at least one optical shape sensor; and
wherein the animation indicating the current spatial positional relationship between the OSS interventional device and the target object comprises an animation indicating the clinical alignment between the OSS interventional device and the target object computed by the display controller.

6. The OSS animated display system of claim 5,
wherein the animation indicating the clinical alignment between the OSS interventional device and the target object computed by the display controller includes one of:
- an inline indicator of the OSS interventional device being aligned with the target object in accordance with an interventional procedure; and
- an outline indicator of the OSS interventional device being misaligned with the target object in accordance with the interventional procedure.

7. The OSS animated display system of claim 1,
wherein the display controller is further configured to compute a clinical depth between the OSS interventional device and the target object defining the current spatial positional relationship between the OSS interventional device and the target object based on the shape of the at least one optical shape sensor; and
wherein the animation indicating the current spatial positional relationship between the OSS interventional device and the target object comprises an animation indicating the clinical depth between the OSS interventional device and the target object computed by the display controller.

8. The OSS animated display system of claim 7,
wherein the animation indicating the clinical depth between the OSS interventional device and the target object computed by the display controller includes one of:
- an in-depth indicator of the OSS interventional device being within a depth range of the target object in accordance with an interventional procedure; and
- an out-of-depth indicator of the OSS interventional device being outside of the depth range of the target object in accordance with the interventional procedure.

9. A display controller for controlling a real-time display on a monitor of an animation indicating a current spatial positional relationship between an optical shape sensing (OSS) interventional device and a previously determined target object, the OSS interventional device including an integration of at least one optical shape sensor and at least one interventional tool, the display controller comprising:
- a processor; and
- a non-transitory memory storing instructions that, when executed by the processor, cause the processor to:
  - derive the animation indicating the current spatial positional relationship between the OSS interventional device and the target object during an interventional procedure from a shape of the at least one optical shape sensor; and
  - control the real-time display on the monitor of a reconstructed shape of the OSS interventional device and the animation indicating the current spatial positional relationship between the OSS interventional device and the target object for tracking position and/or deployment of the OSS interventional device relative to the target object during the interventional procedure.

10. The display controller of claim 9,
wherein the instructions further cause the processor to compute a minimum distance between the OSS interventional device and the target object defining the current spatial positional relationship between the OSS interventional device and the target object based on the shape of the at least one optical shape sensor; and
wherein the animation indicating the current spatial positional relationship between the OSS interventional device and the target object comprises an animation indicating the minimum distance between the OSS interventional device and the target object computed by the display controller.

11. The display controller of claim 10,
wherein the animation indicating the minimum distance between the OSS interventional device and the target object computed by the display controller includes one of:
- an in-plane indicator of the OSS interventional device being in-plane with an imaging of the target object;
- a forward out-of-plane indicator of a forward-facing orientation of the OSS interventional device being out-of-plane with the imaging of the target object;
- a backward out-of-plane indicator of a backward-facing orientation of the OSS interventional device being out-of-plane the imaging of the target object; and
- a contact indicator of a predictive degree of any contact between the OSS interventional device and the target object.

12. The display controller of claim 9,
wherein the instructions further cause the processor to compute a clinical alignment between the OSS interventional device and the target object defining the current spatial positional relationship between the OSS interventional device and the target object based on the shape of the at least one optical shape sensor; and
wherein the animation indicating the current spatial positional relationship between the OSS interventional device and the target object comprises an animation indicating the clinical alignment between the OSS interventional device and the target object computed by the display controller.

13. The display controller of claim 12,
wherein the animation indicating the clinical alignment between the OSS interventional device and the target object computed by the display controller includes one of:
- an inline indicator of the OSS interventional device being aligned with the target object in accordance with an interventional procedure; and
- an outline indicator of the OSS interventional device being misaligned with the target object in accordance with the interventional procedure.

14. The display controller of claim 13,
wherein the instructions further cause the processor to compute a clinical depth between the OSS interventional device and the target object defining the current spatial positional relationship between the OSS interventional device and the target object based on the shape of the at least one optical shape sensor; and
wherein the animation indicating the spatial positional relationship between the OSS interventional device and the target object comprises an animation indicating the clinical depth between the OSS interventional device and the target object computed by the display controller.

15. The display controller of claim 14,
wherein the animation indicating the clinical depth between the OSS interventional device and the target object computed by the display controller includes one of:
- an in-depth indicator of the OSS interventional device being within a depth range of the target object in accordance with an interventional procedure; and
- an out-of-depth indicator of the OSS interventional device being outside of the depth range of the target object in accordance with the interventional procedure.

16. An optical shape sensing (OSS) animated display method for an OSS interventional device, including an integration of at least one optical shape sensor and at least one interventional tool, the OSS animated display method comprising:
- determining a current spatial positional relationship between the OSS interventional device and a previously determined target object during an interventional procedure from a shape of the at least one optical shape sensor;
- deriving an animation indicating the current spatial positional relationship between the OSS interventional device and the target object; and
- displaying in real-time during the interventional procedure a reconstructed shape of the OSS interventional device and the animation indicating the current spatial positional relationship between the OSS interventional device and the target object for tracking position and/or deployment of the OSS interventional device relative to the target object.

17. The OSS animated display method of claim 16,
wherein the target object is one of an anatomical feature, a therapy device or an additional interventional device.

18. The OSS animated display method of claim 16,
wherein determining the current spatial positional relationship between the OSS interventional device and the target object comprises computing a minimum distance between the OSS interventional device and the target object defining the current spatial positional relationship between the OSS interventional device and the target object based on the shape of the at least one optical shape sensor;
wherein the animation of the current spatial positional relationship between the OSS interventional device and the target object includes one of:
- an in-plane indicator of the OSS interventional device being in-plane with an imaging of the target object; and
- a forward out-of-plane indicator of a forward-facing orientation of the OSS interventional device being out-of-plane with the imaging of the target object;
- a backward out-of-plane indicator of a backward-facing orientation of the OSS interventional device being out-of-plane the imaging of the target object; and
- a contact indicator of a predictive degree of any contact between the OSS interventional device and the target object.

19. The OSS animated display method of claim 16,
wherein determining the current spatial positional relationship between the OSS interventional device and the target object comprises computing a clinical alignment between the OSS interventional device and the target object defining the current spatial positional relationship between the OSS interventional device and the target object based on the shape of the at least one optical shape sensor; and
wherein the animation indicating the current spatial positional relationship between the OSS interventional device and the target object includes one of:
- an inline indicator of the OSS interventional device being aligned with the target object in accordance with an interventional procedure; and
- an outline indicator of the OSS interventional device being misaligned with the target object in accordance with the interventional procedure.

20. The OSS animated display method of claim 16,
wherein determining the current spatial positional relationship between the OSS interventional device and the target object comprises computing a clinical depth between the OSS interventional device and the target object defining the current spatial positional relationship between the OSS interventional device and the target object based on the shape of the at least one optical shape sensor; and
wherein the animation indicating the current spatial positional relationship between the OSS interventional device and the target object includes one of:
an in-depth indicator of the OSS interventional device being within a depth range of the target object in accordance with an interventional procedure; and
an out-of-depth indicator of the OSS interventional device being outside of the depth range of the target object in accordance with the interventional procedure.

* * * * *